United States Patent
Kimura et al.

(10) Patent No.: US 7,709,598 B2
(45) Date of Patent: May 4, 2010

(54) FLUORINATED ALKYL FLUOROPHOSHORIC ACID SALTS OF ONIUM AND TRANSITION METAL COMPLEX

(75) Inventors: Hideki Kimura, Kyoto (JP); Jiro Yamamoto, Kyoto (JP); Shinji Yamashita, Kyoto (JP); Mitsuo Kurumaya, Akita (JP); Takaaki Sonoda, Fukuoka (JP)

(73) Assignee: San-Apro Limited, Kyoto-Fu (JP)

( * ) Notice: Subject to any disclaimer, the term of this patent is extended or adjusted under 35 U.S.C. 154(b) by 631 days.

(21) Appl. No.: 11/597,616

(22) PCT Filed: May 27, 2005

(86) PCT No.: PCT/JP2005/009767

§ 371 (c)(1), (2), (4) Date: Nov. 27, 2006

(87) PCT Pub. No.: WO2005/021661

PCT Pub. Date: Mar. 10, 2005

(65) Prior Publication Data

US 2007/0225458 A1    Sep. 27, 2007

(30) Foreign Application Priority Data

May 28, 2004 (JP) .............................. 2004-159921

(51) Int. Cl.
*C08G 59/68* (2006.01)
(52) U.S. Cl. .................... 528/408; 526/179; 549/3; 549/5; 568/9; 556/11
(58) Field of Classification Search ................ 528/409; 526/179; 549/9; 556/11
See application file for complete search history.

(56) References Cited

U.S. PATENT DOCUMENTS

2008/0275224 A1* 11/2008 Ignatyev et al. ............. 534/611

FOREIGN PATENT DOCUMENTS

| JP | 61060724 | * | 3/1986 |
| JP | 9-249676 | | 9/1997 |
| JP | 11-263804 | | 9/1999 |
| WO | 2005/021661 | | 3/2005 |

* cited by examiner

*Primary Examiner*—Randy Gulakowski
*Assistant Examiner*—Shane Fang
(74) *Attorney, Agent, or Firm*—Wenderoth, Lind & Ponack, L.L.P.

(57) ABSTRACT

To obtain a polymerization initiator (acid generating agent) having excellent power for initiation of cationic polymerization without containing arsenic or antimony.

Provided is a specific onium salt or transition metal complex salt of a fluorinated alkyl fluorophosphoric acid.

13 Claims, No Drawings

FLUORINATED ALKYL FLUOROPHOSHORIC ACID SALTS OF ONIUM AND TRANSITION METAL COMPLEX

TECHNICAL FIELD

The present invention relates to novel fluorinated alkyl fluorophosphoric acid salts of onium and transition metal complex, cationic polymerization initiators containing said compounds, curable compositions containing these and cured materials thereof. Specifically, it relates to novel salts of onium and transition metal complex and a fluorophosphate anion having a specific fluoroalkyl group, which are useful as cationic polymerization initiators.

BACKGROUND ART

Salts of onium or transition metal complex are known in prior art as cationic polymerization initiators for curing cationic polymerizable compounds, such as, epoxy compounds by heat or irradiation with active energy beams, such as, by light and electron beam (refer to Patent Reference 1).

In addition, as these salts of onium or transition metal complex produce acids by heat or irradiation with active energy beams are also referred to as acid generators and used in resists and photosensitive materials (refer to Patent Reference 2).

Incidentally, the cationic polymerization initiators described in these specifications contain $BF_4^-$, $PF_6^-$, $AsF_6^-$ and $SbF_6^-$ as anions, cation polymerization initiation capability differs depending on the species of the anion, improving in the order $BF_4^- < PF_6^- < AsF_6^- < SbF_6^-$. However, applications using the cationic polymerization initiators containing $AsF_6^-$ and $SbF_6^-$, which have good polymerization initiation capability, are limited due to the problem of toxicity of As and Sb, such that only $SbF_6^-$ salts are used in limited applications, such as, stereolithography. Therefore, $PF_6^-$ salts, which have poor polymerization initiation capability, are generally used; however, for instance, in order to obtain a curing speed that is on the same order as that of $SbF_6^-$ salts, the addition of nearly 10 times the quantity of the latter is required for $PF_6^-$ salts, and problems exist, such as, loss of physical properties of the cured material due to the large residual amounts of unreacted initiator, solvent used as necessary to dissolve the initiator or decomposition products from the initiator, furthermore, easy corrosion of substrates, equipments and the like due to large amounts of the byproduct HF from the decomposition of the initiator. Therefore, a cationic polymerization initiator not containing a toxic element, having a cationic polymerization initiation capability that is comparable to that of $SbF_6^-$ salts, is strongly sought.

Onium salts or salts of transition metal complex having tetrakis (pentafluorophenyl) borate as anion are proposed as cationic polymerization initiators responding to this problem (refer to Patent Reference 3); however, although the polymerization initiation capability thereof with respect to cationic polymerizable compounds is better than that of those having $PF_6^-$ as anion, it is poorer compared to that of those having $SbF_6^-$ as anion, such that an still better improvement is desired.

[Patent Reference 1] Japanese Patent Application Laid-Open No. S50-151997, Japanese Patent Application Laid-Open No. S50-158680, Japanese Patent Application Laid-Open No. H2-178303, U.S. Pat. No. 4,069,054, idem 4450360, idem 4576999, idem 4640967, Canadian Patent No. 1274646, European Patent Application Disclosure No. 203829

[Patent Reference 2] Japanese Patent Application Laid-Open Nos. H2002-193925, 2001-354669, 2001-294570

[Patent Reference 3] Japanese Patent Application Laid-Open No. H6-184170

SUMMARY OF THE INVENTION

An object of the present invention is to provide a cationic polymerization initiator not containing As and Sb, having a polymerization initiation capability that is comparable to that of a cationic polymerization initiator having $SbF_6^-$ as anion, and having good compatibility with a cationic polymerizable compound, as well as an excellent storage stability for the composition blended with the cationic polymerizable compound.

[Means to Solve the Problems]

As a result of earnest studies to solve the aforementioned problems, the present inventors discovered that salts of an onium or a transition metal complex and a phosphate anion having a specific fluoroalkyl group were excellent cationic polymerization initiators fulfilling these requirements, and reached the present invention.

That is to say, the compounds of the present invention are the onium fluorinated alkyl fluorophosphoric acid salts represented by General Formula (1) and the fluorinated alkyl fluorophosphoric acid salts of transition metal complex represented by General Formula (4).

[Chem. 4]

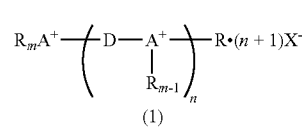

(1)

[In formula (1), A represents an element from Group VIA to Group VIIA (CAS notation) with a valence of m, m representing 1 or 2; n is an integer from 0 to 3, representing the number of repeating units for the structure between parentheses; R represents an organic group bonded to A, and represents an aryl group having 6 to 30 carbon atoms, a heterocyclic group having 4 to 30 carbon atoms, an alkyl group having 1 to 30 carbon atoms, an alkenyl group having 2 to 30 carbon atoms or an alkynyl group having 2 to 30 carbon atoms; furthermore, R may be substituted by at least one species selected from the group comprising each of alkyl, hydroxy, alkoxy, alkyl carbonyl, aryl carbonyl, alkoxy carbonyl, aryloxy carbonyl, arylthio carbonyl, acyloxy, arylthio, alkylthio, aryl, heterocyclic, aryloxy, alkyl sulfinyl, aryl sulfinyl, alkyl sulfonyl, aryl sulfonyl, alkylene oxy, amino, cyano and nitro groups and halogens; the number of R groups is m+n(m−1)+1, and each R may be identical to or different from one another; in addition, two or more R groups may be bonded to one another directly or via —O—, —S—, —SO—, —SO$_2$—, —NH—, —NR'—, —CO—, —COO—, —CONH—, an alkylene group having 1 to 3 carbon atoms or a phenylene group, to form a ring structure containing the element A; herein, R' represents an alkyl group having 1 to 5 carbon atoms or an aryl group having 6 to 10 carbon atoms; D represents a structure represented by the following General Formula (2),

[Chem. 5]

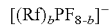

in Formula (2), E represents an alkylene group having 1 to 8 carbon atoms, an arylene group having 6 to 20 carbon atoms or a divalent group of heterocyclic compound having 8 to 20 carbon atoms; furthermore, E is optionally substituted with at least one species chosen from the group comprising each of the alkyl having 1 to 8 carbon atoms, alkoxy having 1 to 8 carbon atoms, aryl having 6 to 10 carbon atoms, hydroxy, cyano and nitro groups and halogens; G represents —O—, —S—, —SO—, —SO$_2$—, —NH—, —NR'—, —CO—, —COO—, —CONH—, an alkylene group having 1 to 3 carbon atoms or a phenylene group; a is an integer from 0 to 5; each of the E groups of a+1 in number and the G groups of a in number may be identical or different; herein, R' is equivalent to the one described above;

X$^-$ is a counter-ion for the onium; the number thereof is n+1 per molecule, among which at least one is a fluorinated alkyl fluorophosphate anion represented by General Formula (3), $$[(Rf)_b PF_{8-b}]^- \quad (3)$$

and the remainder may be another anion; in General Formula (3), Rf represents an alkyl group, of which 80% or more hydrogen atoms are substituted fluorine atoms; b is an integer from 1 to 5 and represents the number thereof; each the Rf groups of b in number may be identical or different.]

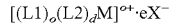

[In Formula (4), M represents one species of transition metal element chosen from Group VIB to Group VIII (CAS notation), L1 and L2 are ligands for the transition metal element M; L1 represents an aromatic compound having 6 to 24 carbon atoms or a heterocyclic compound having 4 to 20 carbon atoms, L2 represents the anion of indene, fluorene or cyclopentadiene, and these L1 and L2 further may be optionally substituted with at least one species chosen from the group consisting each of alkyl, alkoxy, alkylthio, arylthio, alkyl carbonyl, alkoxy carbonyl, phenyl, benzoyl, cyano and nitro groups and halogens; c and d are both integers from 0 to 2 with a total number (c+d) of 2, and respectively represent the number of L1 and L2; if the two ligands are both L1 or both L2, each may be identical with or different from one another; the total electric charge e of the electric charge of ligands L1 and L2 and the electric charge of the transition metal element M is positive and equals to 1 or 2; and X$^-$ has the same meaning as in claim 1.]

[Effect of the Invention]

As the fluorinated alkyl fluorophosphoric acid salts of onium and transition metal complex of the present invention do not contain elements with toxicity problems, such as, arsenic and antimony, they excel on the points of safety and anti-contamination. In addition, the fluorinated alkyl fluorophosphoric acid salts of onium and transition metal complex of the present invention not only has excellent solubility with respect to a cationic polymerizable compound, a composition comprising these and a cationic polymerizable compound has excellent curability by heat or irradiation with active energy beams, such as, by light, electron beam and X-ray, while at the same time has satisfactory storage stability.

BEST MODE FOR CARRYING OUT THE INVENTION

In Formula (1) representing the onium salts of the present invention, A represents an element from Group VIA to Group VIIA (CAS notation), and is bonded to organic groups R and D to form onium [A$^+$]. Among the elements from Group VIA to Group VIIA, S, I and Se, which have excellent cationic polymerization initiation capability, are preferred, S and I being particularly preferred. m represents the valence of element A, and is equal to 1 or 2.

R is an organic group bonded to A, and represents an aryl group having 6 to 30 carbon atoms, a heterocyclic group having 4 to 30 carbon atoms, an alkyl group having 1 to 30 carbon atoms, an alkenyl group having 2 to 30 carbon atoms or an alkynyl group having 2 to 30 carbon atoms, and these may be substituted with at least one species chosen from the group comprising each of alkyl, hydroxy, alkoxy, alkyl carbonyl, aryl carbonyl, alkoxy carbonyl, aryloxy carbonyl, arylthio carbonyl, acyloxy, arylthio, alkylthio, aryl, heterocyclic, aryloxy, alkylsulfinyl, arylsulfinyl, alkyl sulfonyl, aryl sulfonyl, alkylene oxy, amino, cyano and nitro groups and halogens. The number of R groups is m+n(m−1)+1, and each R may be identical to or different from one another. In addition, two or more R groups may be bonded to one another directly or via —O—, —S—, —SO—, —SO$_2$—, —NH—, —NR'—, —CO—, —COO—, —CONH—, an alkylene group having 1 to 3 carbon atoms or a phenylene group, to form a ring structure containing the element A. Herein, R' represents an alkyl group having 1 to 5 carbon atoms or an aryl group having 6 to 10 carbon atoms.

In the above description, as aryl groups having 6 to 30 carbon atoms, monocyclic aryl groups, such as, phenyl group and condensed polycyclic aryl groups, such as, naphthyl, anthracenyl, phenanthrenyl, pyrenyl, chrysenyl, naphthacenyl, benzoanthracenyl, anthraquinolyl, fluorenyl and naphthoquinolyl may be given.

As heterocyclic groups having 4 to 30 carbon atoms, those [groups] that are cyclic and containing 1 to 3 heteroatoms, such as, oxygen, nitrogen and sulfur may be given, these may be identical or different, and monocyclic heterocyclic groups, such as, thienyl, furanyl, pyranyl, pyrrolyl, oxazolyl, thiazolyl, pyridyl, pyrimidinyl and pyrazinyl, and condensed polycyclic heterocyclic groups, such as, indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, cromanyl, isocromanyl, dibenzothienyl, xanthonyl, thioxanthonyl and dibenzofuranyl, may be given as particular examples.

As alkyl groups having 1 to 30 carbon atoms, linear alkyl groups, such as, methyl, ethyl, propyl, butyl, pentyl, octyl, decyl, dodecyl, tetradecyl, hexadecyl and octadecyl, branched alkyl groups, such as, isopropyl, isobutyl, sec-butyl, tert-butyl, isopentyl, neopentyl, tert-pentyl and isohexyl, and cycloalkyl groups, such as, cyclopropyl, cyclobutyl, cyclopentyl and cyclohexyl may be cited.

In addition, as alkenyl groups having 2 to 30 carbon atoms, those] that are linear or branched, such as, vinyl, allyl, 1-propenyl, isopropenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-2-butenyl, 3-methyl-2-butenyl, 1,2-dimethyl-1-propenyl, 1-decenyl, 2-decenyl, 8-decenyl, 1-dodecenyl, 2-dodecenyl and 10-dodecenyl may be cited.

Furthermore, as alkynyl groups having 2 to 30 carbon atoms, those [groups] that are linear or branched, such as, ethynyl, 1-propynyl, 2-propynyl, 1-butynyl, 2-butynyl, 3-butynyl, 1-methyl-1-propynyl, 1-methyl-2-propynyl, 2-methyl-1-propynyl, 2-methyl-2-propynyl, 1-pentynyl, 2-pentynyl, 3-pentynyl, 4-pentynyl, 1-methyl-1-butynyl, 2-methyl-2-butynyl, 3-methyl-2-butynyl, 1,2-dimethyl-1-propynyl, 1-decynyl, 2-decynyl, 8-decynyl, 1-dodecynyl, 2-dodecynyl and 10-dodecynyl may be cited.

The above-mentioned aryl groups having 6 to 30 carbon atoms, heterocyclic groups having 4 to 30 carbon atoms, alkyl groups having 1 to 30 carbon atoms, alkenyl groups having 2 to 30 carbon atoms or alkynyl groups having 2 to 30 carbon atoms, may have at least one species of substituent, and examples of substituents include: linear alkyl groups having 1 to 18 carbon atoms, such as, methyl, ethyl, propyl, butyl, pentyl, octyl, decyl, dodecyl, tetradecyl, hexadecyl and ocdadecyl; branched alkyl groups having 1 to 18 carbon atoms, such as, isopropyl, isobutyl, sec-butyl, tert-butyl, isopentyl, neopentyl, tert-pentyl and isohexyl; cycloalkyl groups having 3 to 18 carbon atoms, such as, cyclopropyl, cyclobutyl, cyclopentyl and cyclohexyl; hydroxyl group; linear or branched alkoxy groups having 1 to 18 carbon atoms, such as, methoxy, ethoxy, propoxy, isopropoxy, butoxy, isobutoxy, sec-butoxy, tert-butoxy, hexyloxy, decyloxy and dodecyloxy; linear or branched alkyl carbonyl groups having 2 to 18 carbon atoms, such as, acetyl, propionyl, butanoyl, 2-methylpropionyl, heptanoyl, 2-methyl butanoyl, 3-methyl butanoyl, octanoyl, decanoyl, dodecanoyl and octadecanoyl; aryl carbonyl groups having 7 to 11 carbon atoms, such as, benzoyl and naphthoyl; linear or branched alkoxy carbonyl groups having 2 to 19 carbon atoms, such as, methoxy carbonyl, ethoxy carbonyl, propoxy carbonyl, isopropoxy carbonyl, butoxy carbonyl, isobutoxy carbonyl, sec-butoxy carbonyl, tert-butoxy carbonyl, octyloxy carbonyl, tetradecyloxy carbonyl and octadecyloxy carbonyl; aryloxy carbonyl groups having 7 to 11 carbon atoms, such as, phenoxy carbonyl and naphthoxy carbonyl; arylthio carbonyl groups having 7 to 11 carbon atoms, such as, phenylthio carbonyl and naphthoxythio carbonyl; linear or branched acyloxy groups having 2 to 19 carbon atoms, such as, acetoxy, ethyl carbonyloxy, propyl carbonyloxy, isopropyl carbonyloxy, butyl carbonyloxy, isobutyl carbonyloxy, sec-butyl carbonyloxy, tert-butyl carbonyloxy, octyl carbonyloxy, tetradecyl carbonyloxy and octadecyl carbonyloxy; arylthio groups having 6 to 20 carbon atoms, such as, phenylthio, 2-methylphenylthio, 3-methylphenylthio, 4-methylphenylthio, 2-chlorophenylthio, 3-chlorophenylthio, 4-chlorophenylthio, 2-bromo phenylthio, 3-bromo phenylthio, 4-bromophenylthio, 2-fluorophenylthio, 3-fluorophenylthio, 4-fluorophenylthio, 2-hydroxyphenylthio, 4-hydroxyphenylthio, 2-methoxyphenylthio, 4-methoxyphenylthio, 1-naphthylthio, 2-naphthylthio, 4-[4-(phenylthio) benzoyl]phenylthio, 4-[4-(phenylthio) phenoxy]phenylthio, 4-[4-(phenylthio) phenyl]phenylthio, 4-(phenylthio) phenylthio, 4-benzoylphenylthio, 4-benzoyl-2-chlorophenylthio, 4-benzoyl-3-chlorophenylthio, 4-benzoyl-3-methylthio phenylthio, 4-benzoyl-2-methylthio phenylthio, 4-(4-methylthiobenzoyl) phenylthio, 4-(2-methylthiobenzoyl) phenylthio, 4-(p-methylbenzoyl) phenylthio, 4-(p-ethylbenzoyl) phenylthio, 4-(p-isopropylbenzoyl) phenylthio and 4-(p-tert-butylbenzoyl) phenylthio; linear or branched alkylthio groups having 1 to 18 carbon atoms, such as, methylthio, ethylthio, propylthio, isopropylthio, butylthio, isobutylthio, sec-butylthio, tert-butylthio, pentylthio, isopentylthio, neopentylthio, tert-pentylthio, octylthio, decylthio and dodecylthio; aryl groups having 6 to 10 carbon atoms, such as, phenyl, tolyl, dimethylphenyl and naphthyl; heterocyclic groups having 4 to 20 carbon atoms, such as, thienyl, furanyl, pyranyl, pyrrolyl, oxazolyl, thiazolyl, pyridyl, pyrimidyl, pyrazinyl, indolyl, benzofuranyl, benzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiynyl, cromanyl, isocromanyl, dibenzothienyl, xanthonyl, thioxanthonyl and dibenzofuranyl; aryloxy groups having 6 to 10 carbon atoms, such as, phenoxy and naphthyloxy; linear or branched alkyl sulfinyl groups having 1 to 18 carbon atoms, such as, methyl sulfinyl, ethyl sulfinyl, propyl sulfinyl, isopropyl sulfinyl, butyl sulfinyl, isobutyl sulfinyl, sec-butyl sulfinyl, tert-butyl sulfinyl, pentyl sulfinyl, isopentyl sulfinyl, neopentyl sulfinyl, tert-pentyl sulfinyl and octyl sulfinyl; aryl sulfinyl groups having 6 to 10 carbon atoms, such as, phenyl sulfinyl, tolyl sulfinyl and naphthyl sulfinyl; linear or branched alkyl sulfonyl groups having 1 to 18 carbon atoms, such as, methyl sulfonyl, ethyl sulfonyl, propyl sulfonyl, isopropyl sulfonyl, butyl sulfonyl, isobutyl sulfonyl, sec-butyl sulfonyl, tert-butyl sulfonyl, pentyl sulfonyl, isopentyl sulfonyl, neopentyl sulfonyl, tert-pentyl sulfonyl and octyl sulfonyl; aryl sulfonyl groups having 6 to 10 carbon atoms, such as, phenyl sulfonyl, tolyl sulfonyl (tosyl group) and naphthyl sulfonyl;

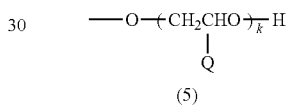

[Chem. 6]

(5)

alkylene oxy groups represented by the General Formula (5) (where Q represents a hydrogen atom or a methyl group, and k is an integer from 1 to 5); unsubstituted amino groups as well as amino groups monosubstituted or disubstitued with an alkyl group having 1 to 5 carbon atoms and/or an aryl group having 6 to 10 carbon atoms (particular examples of alkyl groups having 1 to 5 carbon atoms include: linear alkyl groups, such as, methyl, ethyl, propyl, butyl and pentyl; branched alkyl groups, such as, isopropyl, isobutyl, sec-butyl, tert-butyl, isopentyl, neopentyl and tert-pentyl; cycloalkyl groups, such as, cyclopropyl, cyclobutyl and cyclopentyl; and particular examples of aryl groups having 6 to 10 carbon atoms include: phenyl, naphthyl and the like); cyano group; nitro group; halogens, such as, fluorine, chlorine, bromine and iodine, and the like.

In addition, the following can be given as an example of ring structure containing the element A formed by bonding two or more R groups one to the others directly or via —O—, —S—, —SO—, —SO$_2$—, —NH—, —NR'— (R' represents an alkyl group having 1 to 5 carbon atoms or an aryl group having 6 to 10 carbon atoms; concrete examples of alkyl group having 1 to 5 carbon atoms include, linear alkyl groups, such as, methyl, ethyl, propyl, butyl and pentyl; branched alkyl groups, such as, isopropyl, isobutyl, sec-butyl, tert-butyl, isopentyl, neopentyl and tert-pentyl; cycloalkyl groups, such as, cyclopropyl, cyclobutyl and cyclopentyl; particular examples of aryl groups having 6 to 10 carbon atoms include: phenyl and naphthyl), —CO—, —COO—, —CONH—, an alkylene group having 1 to 3 carbon atoms or a phenylene group.

[Chem. 7]

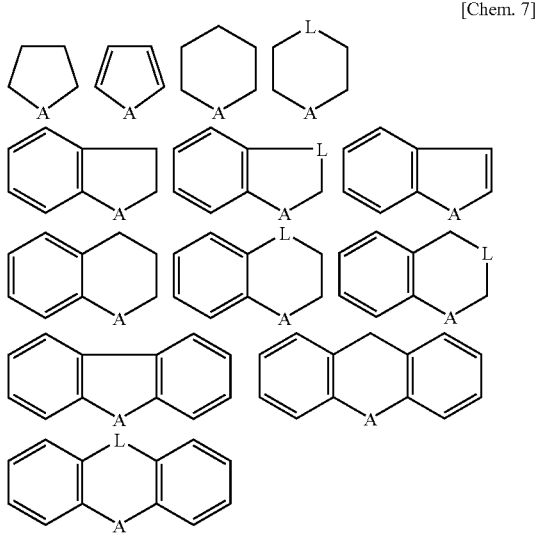

and the like where A represents an element from Group VIA to Group VIIA (CAS notation), L represents —O—, —S—, —SO—, —SO$_2$—, —NH—, —NR'—, —CO—, —COO— and —CONH—; R' has the same meaning as in the foregoing description.]

In Formula (1), the m+n(m−1)+1 R groups that are bonded to the element A from Group VIA to Group VIIA (CAS notation) having a valence of m may be identical to or different from one another; however, at least one of the R groups, furthermore, preferably, all the R groups, are aryl groups having 6 to 30 carbon atoms or heterocyclic groups having 4 to 30 carbon atoms, which may have a previously described substitutent.

In Formula (1), D represents a structure of the following Formula (2) structure,

[Chem. 8]

(2)

in Formula (2), E represents a straight, branched or cyclic alkylene group having 1 to 8 carbon atoms, such as, methylene, ethylene and propylene; an arylene group having 6 to 20 carbon atoms, such as, phenylene, xylylene, naphthylene, biphenylene and anthracenylene; a divalent group of heterocyclic compound having 8 to 20 carbon atoms, such as, dibenzofuran diyl, dibenzothiophene diyl, xanthene diyl, phenoxathiyn diyl, thianthrene diyl, bithiophene diyl, bifuran diyl, thioxanthone diyl, xanthone diyl, carbazole diyl, acridine diyl, phenothiazine diyl and phenazine diyl. Herein, divalent group of heterocyclic compound means a divalent group formed by removing one hydrogen atom from each of two different endocyclic carbon atoms of a heterocyclic compound.

The above alkylene group, arylene group or divalent group of heterocyclic compound may have at least one species of substituent, and particular examples of substituents include: linear alkyl groups having 1 to 8 carbon atoms, such as, methyl, ethyl, propyl, butyl, pentyl and octyl; branched alkyl groups having 1 to 8 carbon atoms, such as, isopropyl, isobutyl, sec-butyl and tert-butyl; cycloalkyl groups having 3 to 8 carbon atoms, such as, cyclopropyl and cyclohexyl; alkoxy groups having 1 to 8 carbon atoms, such as, methoxy, ethoxy, propoxy, butoxy and hexyloxy; aryl group having 6 to 10 carbon atoms, such as, phenyl and naphthyl; hydroxyl group; cyano group; nitro group or halogens, such as, fluorine, chlorine, bromine and iodine.

In Formula (2), G represents —O—, —S—, —SO—, —SO$_2$—, —NH—, —NR'—(R' has the same meaning as described previously), —CO—, —COO—, —CONH—, alkylene groups having 1 to 3 carbon atoms or a phenylene group. Examples of alkylene groups having 1 to 3 carbon atoms include linear or branched alkylene groups, such as, methylene, ethylene and propylene.

In Formula (2), a is an iteger from 0 to 5. Each of the a+1 E groups and a G groups may be identical with or different from one another.

Representative examples of D represented by Formula (2) are shown below.

In case a = 0:

[Chem. 9]

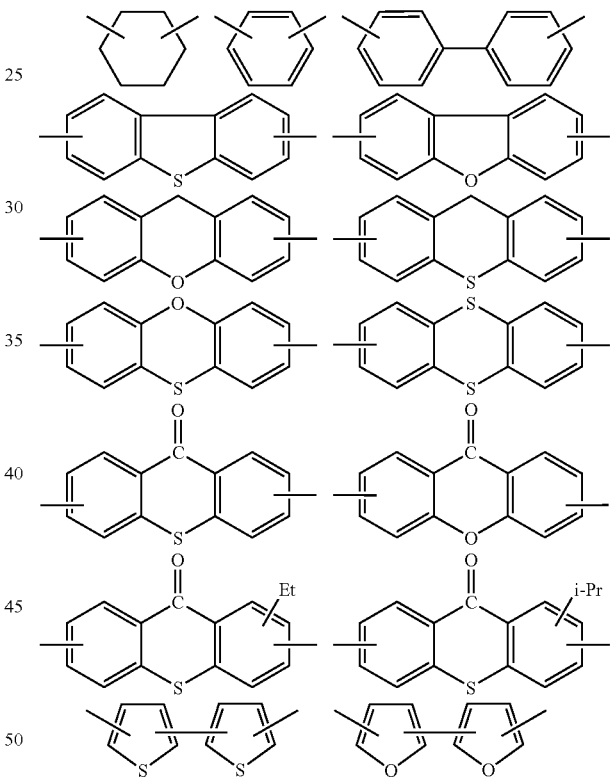

In case a = 1:

[Chem. 10]

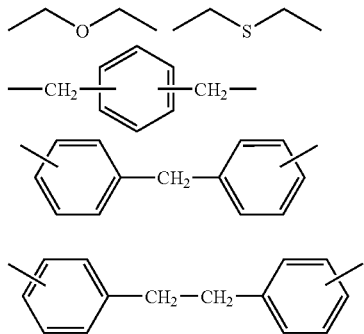

-continued

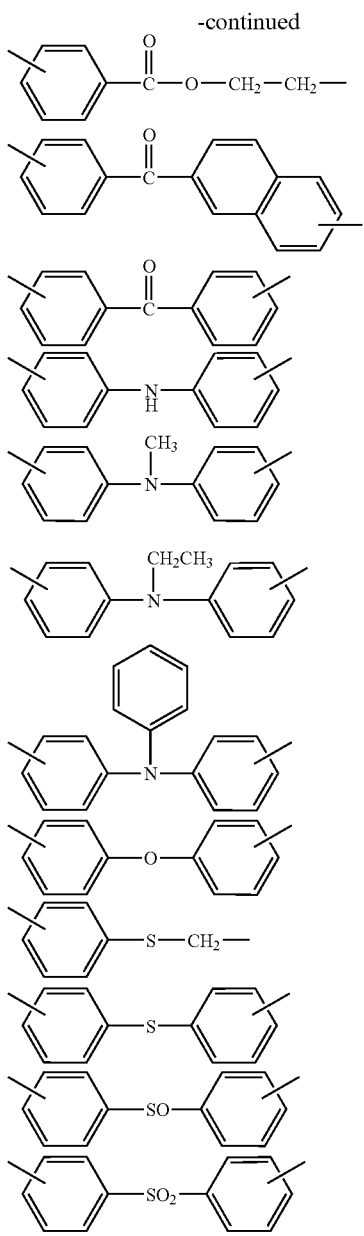

In case a = 2:

[Chem. 11]

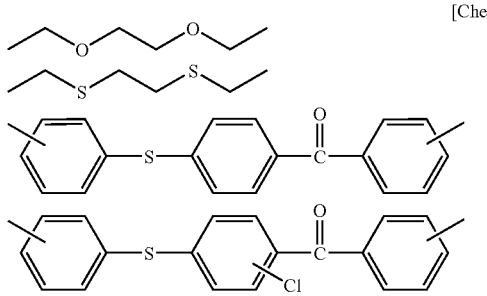

In case a = 3:

[Chem. 12]

-continued

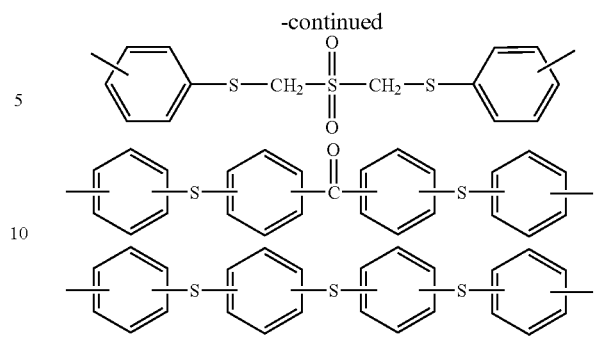

Among these D groups, the groups shown in the following are in particular preferred.

[Chem. 13]

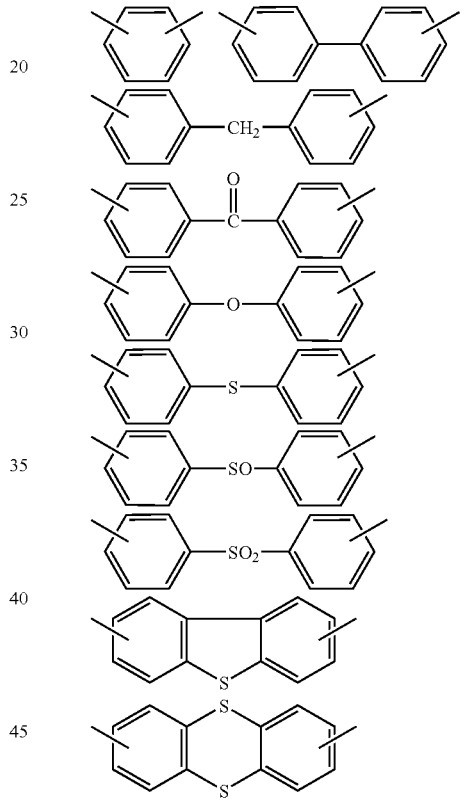

In Formula (1), n is an integer from 0 to 3, preferably 0 or 1, and represents the number of repeating units for a [D–A+ $R_{m-1}$] bond.

Sulfonium, iodonium and selenium are preferred as the onium ion [A+] in Formula (1), and the following representative examples may be given.

Examples of sulfonium ions include: triaryl sulfonium ions, such as, triphenyl sulfonium, tri-p-tolyl sulfonium, tri-o-tolyl sulfonium, tris (4-methoxyphenyl) sulfonium, 1-naphthyldiphenyl sulfonium, 2-naphthyldiphenyl sulfonium, tris (4-fluorophenyl) sulfonium, tri-1-naphthyl sulfonium, tri-2-naphthyl sulfonium, tris (4-hydroxyphenyl) sulfonium, 4-(phenylthio) phenyidiphenyl sulfonium, 4-(p-tolylthio) phenyidi-p-tolyl sulfonium, 4-(4-methoxyphenylthio) phenyl bis(4-methoxyphenyl) sulfonium, 4-(phenylthio) phenyl bis (4-fluorophenyl) sulfonium, 4-(phenylthio) phenyl bis (4-methoxyphenyl) sulfonium, 4-(phenylthio) phenyldi-p-tolyl sulfonium, bis[4-(diphenyl sulfonio) phenyl]sulfide, bis[4-{bis[4-(2-hydroxyethoxy) phenyl]sulfonio} phenyl]sulfide, bis{4-[bis (4-fluorophenyl) sulfonio]phenyl}sulfide, bis{4-[bis (4-methylphenyl) sulfonio]phenyl}sulfide, bis{4-[bis (4-methoxyphenyl) sulfonio]phenyl}sulfide, 4-(4-benzoyl-2-chlorophenylthio) phenyl bis (4-fluorophenyl) sulfonium, 4-(4-benzoyl-2-chlorophenylthio) phenyldiphenyl sulfonium, 4-(4-benzoylphenylthio) phenyl bis (4-fluorophenyl) sulfonium, 4-(4-benzoylphenylthio) phenyldiphenyl sulfonium, 7-isopropyl-9-oxo-10-thia-9,10-dihydro anthracene-2-yldi-p-tolyl sulfonium, 7-isopropyl-9-oxo-10-thia-9,10-dihydro anthracene-2-yldiphenyl sulfonium, 2-[(di-p-tolyl) sulfonio] thioxanthone, 2-[(diphenyl) sulfonio] thioxanthone, 4-[4-(4-tert-butylbenzoyl) phenylthio]phenyidi-p-tolyl sulfonium, 4-[4-(4-tert-butylbenzoyl) phenylthio]phenyldiphenyl sulfonium, 4-[4-(benzoylphenylthio)]phenyldi-p-tolyl sulfonium, 4-[4-(benzoylphenylthio)]phenyldiphenyl sulfonium, 5-(4-methoxyphenyl) thianthrenium, 5-phenylthianthrenium, 5-tolylthianthrenium, 5-(4-ethoxy phenyl) thianthrenium and 5-(2,4,6-trimethylphenyl) thianthrenium; diaryl sulfonium ions, such as, diphenylphenacyl sulfonium, diphenyl(4-nitrophenacyl) sulfonium, diphenylbenzyl sulfonium and diphenylmethyl sulfonium; monoaryl sulfonium ions, such as, phenylmethylbenzyl sulfonium, 4-hydroxyphenylmethylbenzyl sulfonium, 4-methoxyphenylmethylbenzyl sulfonium, 4-aceto carbonyloxy phenylmethylbenzyl sulfonium, 2-naphthylmethylbenzyl sulfonium, 2-naphthylmethyl (1-ethoxy carbonyl) ethyl sulfonium, phenylmethylphenacyl sulfonium, 4-hydroxyphenylmethylphenacyl sulfonium, 4-methoxyphenylmethylphenacyl sulfonium, 4-aceto carbonyloxy phenylmethylphenacyl sulfonium, 2-naphthylmethylphenacyl sulfonium, 2-naphthyl octadecylphenacyl sulfonium and 9-anthracenyl methylphenacyl sulfonium; trialkyl sulfonium ions, such as, dimethylphenacyl sulfonium, phenacyl tetrahydro thiophenium, dimethylbenzyl sulfonium, benzyl tetrahydro thiophenium and octadecylmethylphenacyl sulfonium, and the like; these are described in the following references.

Regarding triaryl sulfonium ions, U.S. Pat. Nos. 4,231,951, 4,256,828, Japanese Patent Application Laid-Open No. H7-61964, Japanese Patent Application Laid-Open No. H8-165290, Japanese Patent Application Laid-Open No. H7-10914, Japanese Patent Application Laid-Open No. H7-25922, Japanese Patent Application Laid-Open No. H8-27208, Japanese Patent Application Laid-Open No. H8-27209, Japanese Patent Application Laid-Open No. H8-165290, Japanese Patent Application Laid-Open No. H8-301991, Japanese Patent Application Laid-Open No. H9-143212, Japanese Patent Application Laid-Open No. H9-278813, Japanese Patent Application Laid-Open No. H10-7680, Japanese Patent Application Laid-Open No. H10-287643, Japanese Patent Application Laid-Open No. H10-245378, Japanese Patent Application Laid-Open No. H8-157510, Japanese Patent Application Laid-Open No. H10-204083, Japanese Patent Application Laid-Open No. H8-245566, Japanese Patent Application Laid-Open No. H8-157451, Japanese Patent Application Laid-Open No. H7-324069, Japanese Patent Application Laid-Open No. H9-268205, Japanese Patent Application Laid-Open No. H9-278935, Japanese Patent Application Laid-Open No. 2001-288205, Japanese Patent Application Laid-Open No. H11-80118, Japanese Patent Application Laid-Open No. H10-182825, Japanese Patent Application Laid-Open No. H10-330353, Japanese Patent Application Laid-Open No. H10-152495, Japanese Patent Application Laid-Open No. H5-239213, Japanese Patent Application Laid-Open No. H7-333834, Japanese Patent Application Laid-Open No. H9-12537, Japanese Patent Application Laid-Open No. H8-325259, Japanese Patent Application Laid-Open No. H8-160606, Japanese Patent Application Laid-Open No. 2000-186071 (U.S. Pat. No. 6,368,769) and the like; regarding diaryl sulfonium, Japanese Patent Application Laid-Open No. H7-300504, Japanese Patent Application Laid-Open No. S64-45357, Japanese Patent Application Laid-Open No. S64-29419 and the like; regarding monoaryl sulfonium, Japanese Patent Application Laid-Open No. H6-345726, Japanese Patent Application Laid-Open No. H8-325225, Japanese Patent Application Laid-Open No. H9-118663 (U.S. Pat. No. 6,093,753), Japanese Patent Application Laid-Open No. H2-196812, Japanese Patent Application Laid-Open No. H2-1470, Japanese Patent Application Laid-Open No. H2-196812, Japanese Patent Application Laid-Open No. H3-237107, Japanese Patent Application Laid-Open No. H3-17101, Japanese Patent Application Laid-Open No. H6-228086, Japanese Patent Application Laid-Open No. H 10-152469, Japanese Patent Application Laid-Open No. H7-300505, Japanese Patent Application Laid-Open No. 2003-277353, Japanese Patent Application Laid-Open No. 2003-277352 and the like; regarding trialkyl sulfonium, Japanese Patent Application Laid-Open No. H4-308563, Japanese Patent Application Laid-Open No. H5-140210, Japanese Patent Application Laid-Open No. H5-140209, Japanese Patent Application Laid-Open No. H5-230189, Japanese Patent Application Laid-Open No. H6-271532, Japanese Patent Application Laid-Open No. S58-37003, Japanese Patent Application Laid-Open No. H2-178303, Japanese Patent Application Laid-Open No. H10-338688, Japanese Patent Application Laid-Open No. H9-328506, Japanese Patent Application Laid-Open No. H11-228534, Japanese Patent Application Laid-Open No. H8-27102, Japanese Patent Application Laid-Open No. H7-333834, Japanese Patent Application Laid-Open No. H5-222167, Japanese Patent Application Laid-Open No. H11-21307, Japanese Patent Application Laid-Open No. H11-35613, U.S. Pat. No. 6,031,014 and the like, may be cited.

Examples of iodonium ions include diphenyl iodonium, di-p-tolyl iodonium, bis (4-dodecylphenyl) iodonium, bis (4-methoxyphenyl) iodonium, (4-octyloxy phenyl) phenyl iodonium, bis (4-decyloxy phenyl) iodonium, 4-(2-hydroxy tetradecyloxy) phenylphenyl iodonium, 4-isopropylphenyl (p-tolyl) iodonium, isobutylphenyl (p-tolyl) iodonium and the like, and these are described in Macromolecules, 10, 1307 (1977), Japanese Patent Application Laid-Open No. H6-184170, U.S. Pat. Nos. 4,256,828, 4,351,708, Japanese Patent Application Laid-Open No. S56-135519, Japanese Patent Application Laid-Open No. S58-38350, Japanese Patent Application Laid-Open No. H10-195117, Japanese Patent Application Laid-Open No. 2001-139539, Japanese Patent Application Laid-Open No. 2000-510516, Japanese Patent Application Laid-Open No. 2000-119306 and the like.

Examples of selenium ions include: triaryl selenium ions, such as, triphenyl selenium, tri-p-tolyl selenium, tri-o-tolyl selenium, tris (4-methoxyphenyl) selenium, 1-naphthyldiphenyl selenium, tris (4-fluorophenyl) selenium, tri-1-naphthyl selenium, tri-2-naphthyl selenium, tris (4-hydroxyphenyl) selenium, 4-(phenylthio) phenyldiphenyl selenium and 4-(p-tolylthio) phenyidi-p-tolyl selenium; diaryl selenium ions, such as, diphenylphenacyl selenium, diphenylbenzyl selenium and diphenylmethyl selenium; monoaryl selenium ions, such as, phenylmethylbenzyl selenium, 4-hydroxyphenylmethylbenzyl selenium, phenylmethylphenacyl selenium, 4-hydroxyphenylmethylphenacyl selenium and 4-methoxyphenylmethylphenacyl selenium; trialkyl selenium ions, such as, dimethylphenacyl selenium, phenacyl tetrahydro selenophenium, dimethylbenzyl selenium, benzyl tetrahydro selenophenium and octadecyl methylphenacyl selenium, and the like; these are described in Japanese Patent Application Laid-Open No. S50-151997, Japanese Patent Application Laid-Open No. S50-151976, Japanese Patent Application Laid-Open No. S53-22597 and the like.

Among these onium ions, sulfonium ions and iodonium ions are preferred, and particularly preferred are sulfonium ions, such as, triphenyl sulfonium, tri-p-tolyl sulfonium, 4-(phenylthio) phenyidiphenyl sulfonium, bis[4-(diphenyl sulfonio) phenyl]sulfide, bis[4-{bis[4-(2-hydroxyethoxy)phenyl]sulfonio}phenyl]sulfide, bis{4-[bis (4-fluorophenyl) sulfonio]phenyl}sulfide, 4-(4-benzoyl-2-chlorophenylthio) phenyl bis (4-fluorophenyl) sulfonium, 4-(4-benzoylphenylthio) phenyldiphenyl sulfonium, 7-isopropyl-9-oxo-10-thia-9,10-dihydro anthracene-2-yldi-p-tolyl sulfonium, 7-isopropyl-9-oxo-10-thia-9,10-dihydro anthracene-2-yl diphenyl sulfonium, 2-[(di-p-tolyl) sulfonio]thioxanthone, 2-[(diphenyl) sulfonio]thioxanthone, 4-[4-(4-tert-butylbenzoyl) phenylthio]phenyldi-p-tolyl sulfonium, 4-[4-(benzoylphenylthio)]phenyidiphenyl sulfonium, 5-(4-methoxyphenyl) thianthrenium, 5-phenylthianthrenium, diphenylphenacyl sulfonium, 4-hydroxyphenylmethylbenzyl sulfonium, 2-naphthylmethyl (1-ethoxy carbonyl) ethyl sulfonium, 4-hydroxyphenylmethylphenacyl sulfonium and octadecylmethylphenacyl sulfonium, as well as iodonium ions, such as, diphenyl iodonium, di-p-tolyl iodonium, bis(4-dodecylphenyl) iodonium, bis (4-methoxyphenyl) iodonium, (4-octyloxy phenyl) phenyl iodonium, bis (4-decyloxy) phenyl iodonium, 4-(2-hydroxy tetradecyloxy) phenylphenyl iodonium, 4-isopropylphenyl (p-tolyl) iodonium and 4-isobutylphenyl (p-tolyl) iodonium.

In Formula (4) representing the fluorinated alkyl fluorophosphoric acid salt of transition metal complex of the present invention, ligand L1 represents an aromatic compound having 6 to 24 carbon atoms or a heterocyclic compound having 4 to 20 carbon atoms containing mainly 1 to 3 heteroatoms, such as, oxygen, nitrogen and sulfur; these may be identical or different.

Examples of aromatic compounds having 6 to 24 carbon atoms include monocyclic aromatic compounds, such as, benzene, and condensed polycyclic aromatic compounds, such as, naphthalene, anthracene, phenanthrene, pyrene, chrysene, naphthacene, benzoanthracene, anthraquinone, naphthoquinone, indene, biphenylene, fluorene, triphenylene and coronene.

Examples of heterocyclic compounds having 4 to 20 carbon atoms include monocyclic aromatic compounds such as thiophene, furan, pyran, pyrrole, oxazole, thiazole, pyridine, pyrimidine and pyrazine, and condensed polycyclic aromatic compounds, such as, indole, benzofuran, benzo thiophene, quinoline, isoquinoline, quinoxaline, quinazoline, carbazole, acridine, phenothiazine, phenazine, xanthene, thianthrene, phenoxazine, phenoxathiin, chroman, isochroman, dibenzo thiophene, xanthone, thioxanthone and dibenzofuran.

These aromatic compounds or heterocyclic compounds may be substituted with at least one species chosen from the substituents below, and examples of the substituents include: linear alkyl groups having 1 to 12 carbon atoms, such as, methyl, ethyl, propyl, butyl, pentyl, octyl and decyl; branched alkyl groups having 1 to 12 carbon atoms, such as, isopropyl, isobutyl, sec-butyl, tert-butyl, isopentyl, neopentyl, tert-pentyl and isohexyl; cycloalkyl groups having 3 to 6 carbon atoms, such as, cyclopropyl, cyclobutyl, cyclopentyl and cyclohexyl; linear and branched alkoxy groups having 1 to 6 carbon atoms, such as, methoxy, ethoxy, propoxy, isopropoxy, butoxy, isobutoxy, sec-butoxy, tert-butoxy and hexyloxy; linear and branched alkylthio groups having 1 to 6 carbon atoms, such as, methylthio, ethylthio, propylthio, isopropylthio, butylthio, isobutylthio, sec-butylthio and tert-butylthio; arylthio groups having 6 to 12 carbon atoms, such as, phenylthio and naphthylthio groups; linear and branched alkyl carbonyl groups having 2 to 7 carbon atoms, such as, acetyl, propionyl, butanoyl, 2-methylpropionyl, heptanoyl, 2-methyl butanoyl and 3-methyl butanoyl; linear and branched alkoxy carbonyl group having 2 to 7 carbon atoms, such as, methoxy carbonyl, ethoxy carbonyl, propoxy carbonyl, isopropoxy carbonyl, butoxy carbonyl, isobutoxy carbonyl, sec-butoxy carbonyl and tert-butoxy carbonyl; halogens, such as, fluorine, chlorine, bromine and iodine; phenyl group; benzoyl group; cyano group or nitro group, and the like.

Concrete examples of aromatic compounds containing the above-mentioned substituents include toluene, xylene, ethylbenzene, cumene, mesitylene, methoxy benzene, ethoxy benzene, 1,2-dimethoxy benzene, 1,3-dimethoxy benzene, 1,4-dimethoxy benzene, 1,3,5-trimethoxy benzene, acetylbenzene, chlorobenzene, 1,2-dichlorobenzene, 1,3-dichlorobenzene, 1,4-dichlorobenzene, 2-chlorotoluene, 3-chlorotoluene, 4-chlorotoluene, bromobenzene, 1,2-dibromobenzene, 1,3-dibromobenzene, 1,4-dibromobenzene, 2-bromo toluene, 3-bromo toluene, 4-bromo toluene, 1-methyl naphthalene, 2-methyl naphthalene, 1-methoxy naphthalene, 2-methoxy naphthalene, 1-chloronaphthalene, 2-chloronaphthalene, 1-bromo naphthalene, 2-bromo naphthalene, biphenyl, diphenyl ether, diphenyl sulfide, triphenylene and the like.

Anion of indene, fluorene or cyclopentadiene may be cited as the ligand L2 in Formula (4) representing the fluorinated alkyl fluorophosphoric acid salt of transition metal complex of the present invention. If two ligands L2 are present, they may be identical or different.

These may be substituted with at least one species of substituent that is identical to the case of ligand L1 mentioned above, and examples thereof include: anions of indene derivatives, such as, 2-methyl indene, 2-ethyl indene, 4-methyl indene and 4-chloro indene; anions of fluorene derivatives, such as, 1-methylfluorene, 4-methylfluorene, 4-methoxyfluorene and 1-chlorofluorene; anions of cyclopentadiene derivatives, such as, methyl cyclopentadiene, pentamethyl cyclopentadiene, phenyl cyclopentadiene and chloro cyclopentadiene.

In Formula (4), M represents one species of transition metal element from Group VIB to Group VIII (CAS notation), and Cr, Mo, W, Mn, Fe or Co and the like may be cited. Among these, Fe is preferred.

As transition metal complex cations represented in General Formula (4), for instance, Cr compounds, such as, ($\eta^5$-cyclopentadienyl) ($\eta^6$-toluene) $Cr^+$, ($\eta^5$-cyclopentadienyl) ($\eta^6$-xylene) $Cr^+$, ($\eta^5$-cyclopentadienyl) ($\eta^6$-1-methyl naphthalene) $Cr^+$, ($\eta^5$-cyclopentadienyl) ($\eta^6$-cumene) $Cr^+$, ($\eta^5$-cyclopentadienyl) ($\eta^6$-mesitylene) $Cr^+$, ($\eta^5$-cyclopentadienyl) ($\eta^6$-pyrene) $Cr^+$, ($\eta^5$-fluorenyl) ($\eta^6$-cumene) $Cr^+$, ($\eta^5$-indenyl) ($\eta^6$-cumene) $Cr^+$, bis ($\eta^6$-mesitylene) $Cr^{2+}$, bis ($\eta^6$-xylene) $Cr^+$, bis ($\eta^6$-cumene) $Cr^{2+}$, bis ($\eta^6$-toluene) $Cr^{2+}$, ($\eta^6$-toluene) ($\eta^6$-Xylene) $Cr^{2+}$, ($\eta^6$-cumene) ($\eta^6$-naphthalene) $Cr^{2+}$, bis ($\eta^5$-cyclopentadienyl) $Cr^+$, bis ($\eta^5$-indenyl) $Cr^+$, ($\eta^5$-cyclopentadienyl) ($\eta^5$-fluorenyl) $Cr^+$ and ($\eta^5$-cyclopentadienyl) ($\eta^5$-indenyl) $Cr^+$, furthermore, Fe compounds, such as, ($\eta^5$-cyclopentadienyl) ($\eta^6$-toluene) $Fe^+$, ($\eta^5$-cyclopentadienyl) ($\eta^6$-xylene) $Fe^+$, ($\eta^5$-cyclopentadienyl) ($\eta^6$-1-methyl naphthalene) $Fe^+$, ($\eta^5$-cyclopentadienyl) ($\eta^6$-cumene) $Fe^+$, ($\eta^5$-cyclopentadienyl) ($\eta^6$-mesitylene) $Fe^+$, ($\eta^5$-cyclopentadienyl) ($\eta^6$-pyrene) $Fe^+$, ($\eta^5$-fluorenyl) ($\eta^6$-cumene) $Fe^+$, ($\eta^5$-indenyl) ($\eta^6$-cumene) $Fe^+$, bis($\eta^6$-mesitylene) $Fe^{2+}$, bis ($\eta^6$-xylene) $Fe^{2+}$, bis($\eta^6$-cumene) $Fe^{2+}$, bis($\eta^6$-toluene) $Fe^{2+}$, ($\eta^6$-toluene) ($\eta^6$-Xylene) $Fe^{2+}$, ($\eta^6$-cumene) ($\eta^6$-naphthalene) $Fe^{2+}$, bis($\eta^5$-cyclopentadienyl) $Fe^{2+}$, bis($\eta^5$-indenyl) $Fe^+$, ($\eta^5$-cyclopentadienyl) ($\eta^5$-fluorenyl) $Fe^+$ and ($\eta^5$-cyclopentadienyl) ($\eta^5$-indenyl) $Fe^+$, may be cited.

These are described in Macromol. Chem., 81, 86 (1965), Angew. Makromol. Chem., 50, 9 (1976), Macromol. Chem., 153, 229 (1972), J. Polym. Sci., Polym. Chem. Edn., 14, 1547 (1976), Chem. Ztg., 108, 345 (1984), J. Imaging. Sci., 30, 174 (1986), J. Photochem. Photobiol. A: Chem., 77 (1994), J. Rad. Curing., 26 (1986), Adv. Polym. Sci., 78, 61 (1986), U.S. Pat. No. 4,973,722, idem 4992572, idem 3895954, European Patent Disclosure 203829, idem 354181, idem 94914, idem 109851, idem 94915, Japanese Patent Application Laid-Open No. S58-210904 (U.S. Pat. No. 4,868,288), Japanese Patent Application Laid-Open No. S59-108003, Japanese Patent Application Laid-Open No. 2000-226396, Japanese Patent Application Laid-Open No. H2-284903 and the like.

Among the above-mentioned transition metal complex cations, preferred are ($\eta^5$-cyclopentadienyl) ($\eta^6$-toluene) $Fe^+$, ($\eta^5$-cyclopentadienyl) ($\eta^6$-xylene) $Fe^+$, ($\eta^5$-cyclopentadienyl) ($\eta^6$-1-methyl naphthalene) $Fe^+$, ($\eta^5$-cyclopentadienyl) ($\eta^6$-cumene) $Fe^+$, ($\eta^5$-cyclopentadienyl) ($\eta^6$-mesitylene) $Fe^+$, ($\eta^5$-cyclopentadienyl) ($\eta^6$-pyrene) $Fe^+$, ($\eta^5$-fluorenyl) ($\eta^6$-cumene) $Fe^+$, ($\eta^5$-indenyl) ($\eta^6$-cumene) $Fe^+$, bis ($\eta^6$-mesitylene) $Fe^{2+}$, bis ($\eta^6$-xylene) $Fe^{2+}$, bis ($\eta^6$-cumene) $Fe^{2+}$, ($\eta^6$-toluene) ($\eta^6$-xylene) $Fe^{2+}$, ($\eta^6$-cumene) ($\eta^6$-naphthalene) $Fe^{2+}$, bis ($\eta^5$-cyclopentadienyl) $Fe^+$, bis ($\eta^5$-indenyl) $Fe^+$, ($\eta^5$-cyclopentadienyl) ($\eta^5$-fluorenyl) $Fe^+$ and ($\eta^5$-cyclopentadienyl) ($\eta^5$-indenyl) $Fe^+$.

In Formula (1) and Formula (4) representing the fluorinated alkyl fluorophosphoric acid salts of onium and transition metal complex of the present invention, $X^-$ is a counter-ion. The number thereof in Formula (1) is n+1 per molecule, in addition, the number thereof in Formula (4) is e per molecule, among which at least one is a fluorinated alkyl fluorophosphate anion represented by Formula (3), and the remainder may be other anions.

The other anions may be any anions well known in prior art, for instance, halogen ions, such as, $F^-$, $Cl^-$, $Br^-$ and $I^-$; $OH^-$; $ClO_4^-$; sulfonic acid ions, such as, $FSO_3^-$, $ClSO_3^-$, $CH_3SO_3^-$, $C_6H_5SO_3^-$ and $CF_3SO_3^-$; sulfuric acid ions, such as, $HSO_4^-$ and $SO_4^{2-}$; carbonic acid ions, such as, $HCO_3^-$ and $CO_3^{2-}$; phosphoric acid ions, such as, $H_2PO_4^-$, $HPO_4^{2-}$ and $PO_4^{3-}$; fluorophosphoric acid ions, such as, $PF_6^-$ and $PF_5OH^-$; boric acid ions, such as, $BF_4^-$, $B(C_6F_5)_4^-$ and $B(C_6H_4CF_3)_4^-$; $AlCl_4^-$; $BiF_6^-$ and the like. In addition to these, fluoroantimonic acid ions, such as $SbF_6^-$ and $SbF_5OH$, or fluoroarsenic acid ions, such as, $AsF_6^-$ and $AsF_5OH^-$ can be cited; however, they are not preferred as they contain toxic elements.

In the fluorinated alkyl fluorophosphate anion represented in Formula (3), Rf represents an alkyl group substituted by a fluorine atom, the preferred number of carbon atoms being 1 to 8, and a more preferred number of carbon atoms being 1 to 4. Particular examples of alkyl group include: linear alkyl groups, such as, methyl, ethyl, propyl, butyl, pentyl and octyl; branched alkyl groups, such as, isopropyl, isobutyl, sec-butyl and tert-butyl; furthermore, cycloalkyl groups, such as, cyclopropyl, cyclobutyl, cyclopentyl and cyclohexyl and the like; the proportion of hydrogen atoms in the alkyl group replaced by fluorine atoms being, in general, 80% or more, preferably 90% or more, and more preferably 100%. If the fluorine atom substitution ratio is smaller than 80%, the cationic polymerization initiation capability of the salts of onium and transition metal complex of the present invention decreases.

A particularly preferred Rf is a linear or branched perfluoroalkyl group having 1 to 4 carbon atoms with a fluorine atom substitution ratio of 100%, and particular examples include $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $(CF_3)_3C$.

In Formula (3), b, the number of Rf groups, is an integer from 1 to 5, preferably from 2 to 4, and particularly preferably 2 or 3. Each of the b Rf groups may be identical or different.

Particular examples of preferred fluorinated alkyl fluorophosphate anions include $[(CF_3CF_2)_2PF_4]^-$, $[(CF_3CF_2)_3PF_3]^-$, $[((CF_3)_2CF)_2PF_4]^-$, $[((CF_3)_2CF)_3PF_3]^-$, $[(CF_3CF_2CF_2)_2PF_4]^-$, $[(CF_3CF_2CF_2)_3PF_3]^-$, $[((CF_3)_2CFCF_2)_2PF_4]^-$, $[((CF_3)_2CFCF_2)_3PF_3]^-$, $[(CF_3CF_2CF_2CF_2)_2PF_4]^-$ and $[(CF_3CF_2CF_2)_3PF_3]^-$, and among these, $[(CF_3CF_2)_3PF_3]^-$, $[(CF_3CF_2CF_2)_3PF_3]^-$, $[((CF_3)_2CF)_3PF_3]^-$, $[((CF_3)_2CF)_2PF_4]^-$, $[((CF_3)_2CFCF_2)_3PF_3]^-$ and $[((CF_3)_2CFCF_2)_2PF_4]^-$ are particularly preferred.

The fluorinated alkyl fluorophosphoric acid salt of onium or transition metal complex of the present invention can be prepared by the metathesis method. The metathesis method is described in, for instance, Shin Jikken Kagaku Koza Volume 14-I (1978, Maruzen) p-448; Advance in Polymer Science, 62, 1-48 (1984); Shin Jikken Kagaku Koza Volume 14-III (1978, Maruzen) p1838-1846; Organic Chemistry of Sulfur (Synthesis Reaction Edition, 1982, Kagaku Dojin), Chapter 8, p237-280; Nippon Kagaku Zasshi, 87, (5), 74 (1966); J. Org. Chem., 32, 2580 (1967); Tetrahedron Letters, 36, 3437 (1973); Bulletin de la Societe Chimique de France, 1, 228 (1976); Bulletin de la Societe Chimique de France 11, 2571 (1975); Inorg. Chem., 10, 1559 (1971); Chem. Ber., 93, 2729 (1960); J. Organomet. Chem., 54, 255 (1973); "Organometallic Syntheses", vol. 1, Academic Press, P138 (1965); Tetrahedron, 39, 4027 (1983); J. Amer. Chem. Soc., 103, 758 (1981); J. Chem. Soc., Chem. Commun., 1971, 930 (1971); J. Amer. Chem. Soc., 92, 7207 (1970); Japanese Patent Application Laid-Open No. S64-45357, Japanese Patent Application Laid-Open No. S61-212554, Japanese Patent Application Laid-Open No. S61-100557, Japanese Patent Application Laid-Open No. H5-4996, Japanese Patent Application Laid-Open No. H7-82244, Japanese Patent Application Laid-Open No. H7-82245, Japanese Patent Application Laid-Open No. S58-210904, Japanese Patent Application Laid-Open No. H6-184170 and the like; however, first, a halogen ion salt, such as, of $F^-$, $Cl^-$, $Br^-$ or $I^-$; an $OH^-$ salt; a $ClO_4^-$ salt; a salt with a sulfonic acid ion, such as, $FSO_3^-$, $ClSO_3^-$, $CH_3SO_3^-$, $C_6H_5SO_3^-$ and $CF_3SO_3^-$; a salt with a sulfuric acid ion, such as, $HSO_4^-$ and $SO_4^{2-}$; a salt with a carbonic acid ion, such as, $HCO_3^-$ and $CO_3^{2-}$; a salt with a phosphoric acid ion, such as, $H_2PO_4^-$, $HPO_4^{2-}$ and $PO_4^{3-}$, and the like, of onium or transition metal complex is prepared, this is added to an aqueous solution containing an alkaline metal salt of fluorinated alkyl fluorophosphate anion represented in Formula (3), an alkaline earth metal salt or a quarternary ammonium salt, and, as necessary, another anionic constituent, such as, $KPF_6$, $KBF_4$ and $LiB (C_6F_5)_4$ in theoretical amounts or more, and subjected to metathesis. As the salt of the present invention thus generated, separates in a crystalline or oil form, crystals can be recovered by filtration, and those in the fluid form can be recovered by liquid separation or by extraction with an adequate solvent. The salt of onium or transition metal complex of the present invention obtained in this way, can be purified by methods, such as recrystallization or washing with water and solvents, as necessitated.

The structure of the fluorinated alkyl fluorophosphoric acid salts of onium and transition metal complex obtained in this way can be identified by conventional analytical procedures such as, for instance, respective nuclear magnetic resonance spectra of $^1H$, $^{13}C$, $^{19}F$ and $^{13}P$, infrared absorption spectrum or elemental analysis, and so on.

A salt of alkali metal is preferred as the fluorinated alkyl fluorophosphoric acid salt used in the above-mentioned metathesis reaction. This salt is obtained by reacting the precursor fluorinated alkyl fluorophosphorane and a fluorinated alkali metal in an aprotic solvent, such as, dimethyl ether, diethoxy ethane, acetonitrile or a mixture thereof, at −35 to 60° C. (U.S. Pat. No. 6,210,830).

The precursor fluorinated alkyl fluorophosphorane is obtained by, for instance, a method whereby an alkyl phosphine is fluorinated electrochemically by hydrofluoric acid under atmospheric pressure at a temperature of −15 to 20° C. (U.S. Pat. No. 6,264,818), and the like. The proceeding of electrochemical fluorination is proportional to the quantity of electricity, and the fluorination is terminated, in general, at a moment when 90 to 150%, or in particular 110 to 130%, of the theoretical quantity of electricity has been consumed. In this way, a fluorinated alkyl fluorophosphorane in which 80% or more, preferably 90% or more, of the hydrogen atoms of the alkyl group are substituted by fluorine, is obtained. As the target fluorinated alkyl fluorophosphorane separates from the electrolytic solution, it can be recovered by liquid separation, and purified by distillation, if necessary.

The fluorinated alkyl fluorophosphoric acid salts of onium and transition metal complex of the present invention can be used alone, or applied by combining two or more species, as a cationic polymerization initiator. In addition, they can be applied by combining with another cationic polymerization initiator well known in prior art. Examples of other cationic initiators include, for instance, salts of onium ions, such as, sulfonium, iodonium, selenium, ammonium and phosphonium or transition metal complex ions and various anions, examples of anion including: halogen ions, such as, $F^-$, $Cl^-$, $Br^-$ and $I^-$; $OH^-$; $ClO_4^-$; sulfonic acid ions, such as, $FSO_3^-$, $ClSO_3^-$, $CH_3SO_3^-$, $C_6H_5SO_3^-$ and $CF_3SO_3^-$; sulfuric acid ions, such as, $HSO_4^-$ and $SO_4^{2-}$; carbonic acid ions, such as, $HCO_3^-$ and $CO_3^{2-}$; $H_2PO_4^-$, phosphoric acid ions, such as, $HPO_4^{2-}$ and $PO_4^{3-}$; fluorophosphoric acid ions, such as, $PF_6^-$ and $PF_5OH^-$; boric acid ions, such as, $BF_4^-$, $B(C_6F_5)_4^-$ and $B(C_6H_4CF_3)_4^-$; $AlCl_4^-$; $BiF_6^-$; fluoroantimonic acid ions, such as, $SbF_6^-$ and $SbF_5OH^-$; fluoroarsenic acid ions, such as, $AsF_6^-$ and $AsF_5OH^-$, and the like. Furthermore, they may be applied by combining with a fluorinated alkyl fluorophosphoric acid salt of ammonium or phosphonium, and the like, with the proviso that fluoroantimonic acid ions and fluoroarsenic acid ions are not preferred as they contain toxic elements.

The above-mentioned sulfonium ions, iodonium ions or selenium ions include all those that are well known, and representative examples and reference literature thereof are mentioned in the present specification.

Examples of the above-mentioned ammonium ions include, for instance, tetraalkyl ammonium ions, such as, tetramethyl ammonium, ethyltrimethyl ammonium, diethyidimethyl ammonium, triethylmethyl ammonium, tetraethyl ammonium, trimethyl-n-propyl ammonium, trimethyl isopropyl ammonium, trimethyl-n-butyl ammonium, trimethyl isobutyl ammonium, trimethyl-tert-butyl ammonium, trimethyl-n-hexyl ammonium, dimethyldi-n-propyl ammonium, dimethyl diisopropyl ammonium, dimethyl-n-propyl isopropyl ammonium, methyl tri-n-propyl ammonium and methyl triisopropyl ammonium; pyrrolidinium ions, such as, N,N-dimethyl pyrrolidinium, N-ethyl-N-methyl pyrrolidinium and N,N-diethyl pyrrolidinium; imidazolinium, such as, N,N'-dimethylimidazolinium, N,N'-diethyl imidazolinium, N-ethyl-N'-methylimidazolinium, 1,2,3-trimethylimidazolinium, 1,3,4-trimethylimidazolinium, 1,3-diethyl-2-methylimidazolinium, 1,3-diethyl-4-methylimidazolinium and 1,2,3,4-tetramethylimidazolinium; tetrahydropyrimidium such as, N,N'-dimethyl tetrahydropyrimidinium, N,N'-diethyl tetrahydropyrimidinium, N-ethyl-N'-methyl tetrahydropyrimidinium and 1,2,3-trimethyl tetrahydropyrimidinium; morpholinium ions, such as, N,N'-dimethyl morpholinium, N-ethyl-N-methyl morpholinium and N,N-diethyl morpholinium; piperidinium ions, such as, N,N-dimethyl piperidinium, N-ethyl-N'-methyl piperidinium and N,N'-diethyl piperidinium; pyridinium ions, such as, N-methyl pyridinium, N-ethyl pyridinium, N-n-propyl pyridinium, N-isopropyl pyridinium, N-n-butyl pyridinium, N-benzyl pyridinium and N-phenacyl pyridium; imidazolium ions, such as, N,N'-dimethyl imidazolium, N-ethyl-N-methyl imidazolium, N,N'-diethyl imidazolium, 1,2-diethyl-3-methyl imidazolium, 1,3-diethyl-2-methyl imidazolium and 1-methyl-3-n-propyl-2,4-dimethyl imidazolium; quinolium ions, such as, N-methyl quinolium, N-ethyl quinolium, N-n-propyl quinolium, N-isopropyl quinolium, N-n-butyl quinolium, N-benzyl quinolium and N-phenacyl quinolium; isoquinolium ions, such as, N-methyl isoquinolium, N-ethyl isoquinolium, N-n-propyl isoquinolium, N-isopropyl isoquinolium, N-n-butyl isoquinolium, N-benzyl isoquinolium and N-phenacyl isoquinolium; thiazonium ions, such as, benzyl benzothiazonium and phenacyl benzothiazonium; acrydium ions, such as, benzyl acrydium and phenacyl acrydium.

These are described in U.S. Pat. No. 4,069,055, Patent No. 2519480, Japanese Patent Application Laid-Open No. H5-222112, Japanese Patent Application Laid-Open No. H5-2221 11, Japanese Patent Application Laid-Open No. H5-262813, Japanese Patent Application Laid-Open No. H5-255256, Japanese Patent Application Laid-Open No. H7-109303, Japanese Patent Application Laid-Open No. H10-101718, Japanese Patent Application Laid-Open No. H2-268173, Japanese Patent Application Laid-Open No. H9-328507, Japanese Patent Application Laid-Open No. H5-132461, Japanese Patent Application Laid-Open No. H9-221652, Japanese Patent Application Laid-Open No. H7-43854, Japanese Patent Application Laid-Open No. H7-43901, Japanese Patent Application Laid-Open No. H5-262813, Japanese Patent Application Laid-Open No. H4-327574, Japanese Patent Application Laid-Open No. H2-43202, Japanese Patent Application Laid-Open No. S60-203628, Japanese Patent Application Laid-Open No. S57-209931, Japanese Patent Application Laid-Open No. H9-221652 and the like.

Examples of the above-mentioned phosphonium ion include, for instance, tetraaryl phosphonium ions, such as, tetraphenyl phosphonium, tetra-p-tolyl phosphonium, tetrakis(2-methoxyphenyl) phosphonium, tetrakis(3-methoxyphenyl) phosphonium and tetrakis(4-methoxyphenyl) phosphonium; triaryl phosphonium ions, such as, triphenylbenzyl phosphonium, triphenylphenacyl phosphonium, triphenylmethyl phosphonium and triphenyl butyl phosphonium; tetraalkyl phosphonium ions, such as, triethylbenzyl phosphonium, tributylbenzyl phosphonium, tetraethyl phosphonium, tetrabutyl phosphonium, tetrahexyl phosphonium, triethylphenacyl phosphonium and tributylphenacyl phosphonium, and the like. These are described in Japanese Patent Application Laid-Open No. H6-157624, Japanese Patent Application Laid-Open No. H5-105692, Japanese Patent Application Laid-Open No. H7-82283, Japanese Patent Application Laid-Open No. H9-202873 and the like.

Representative examples and reference literature of the above-mentioned transition metal complex ions are mentioned in the present specification.

When combining two or more species of the fluorinated alkyl fluorophosphoric acid salts of onium and transition metal complex of the present invention in an application, the proportions can be as desired and not limited.

The proportions in use when combining another cationic polymerization initiator for an application may be arbitrary; however, usually, the other cationic polymerization initiator is 10 to 900 parts by mass, preferably 25 to 400 parts by mass, per 100 parts by mass of fluorinated alkyl fluorophosphoric acid salts of onium and/or transition metal complex of the present invention (in the descriptions hereinafter, parts represents parts in mass).

The cationic polymerization initiators of the present invention may be dissolved beforehand in solvents that do not inhibit cationic polymerization to facilitate dissolution into cationic polymerizable compounds, and examples of the solvents include, for instance, carbonates, such as, propylene carbonate, ethylene carbonate, 1,2-butylene carbonate, dimethyl carbonate and diethyl carbonate; esters such as ethyl acetate, ethyl lactate, β-propiolactone, β-butyrolactone, γ-butyrolactone, δ-valerolactone and ε-caprolactone; monoalkyl ethers of glycols, such as, ethylene glycol, propylene glycol, diethylene glycol, dipropylene glycol, triethylene glycol and tripropylene glycol, for instance, monomethyl ether, monoethyl ether, monobutyl ether; or dialkyl ethers, for instance, dimethyl ether, diethyl ether, dibutyl ether, furthermore, glycols, such as, acetate ester of the aforementioned monoalkyl ethers, and the like.

When using these solvents, the proportions used are, usually, 15 to 1000 parts, and preferably 30 to 500 parts, of solvents per 100 parts of the cationic polymerization initiator of the present invention.

The curable composition in the present invention is constituted of the cationic polymerization initiator of the present invention and the cationically polymerizable compounds.

Examples of the cationically polymerizable compounds to which the fluorinated alkyl fluorophosphoric acid salts of onium and transition metal complex of the present invention, or a cationic polymerization initiator comprising these and another cationic polymerization initiator are applicable include, for instance, cyclic ester compounds, such as, epoxides and oxetanes, ethylenic unsaturated compounds, such as, vinyl ethers and styrene, and furthermore, bicyclo orthoesters, spiro orthocarbonates, spiro orthoesters and the like.

Examples of epoxides include those well known in prior art; aromatic epoxides, that is, glycidyl ethers of monohydric and polyhydric phenols having at least one aromatic ring, for instance, phenol, biphenol, bisphenol A, bisphenol F, phenol novolacs, cresol novolacs and brominated products thereof or glycidyl ethers of compounds resulting from further adding alkylene oxide thereto, as well as glycidyl esters of monovalent and multivalent carboxylic acids having an aromatic ring, for instance, diglycidyl phthalate, diglycidyl-3-methyl phthalate and the like; alicyclic epoxides, that is to say, compounds obtained by epoxidizing with an oxidizing agent a compound having at least one cyclohexene or cyclopentene ring, for instance, 3,4-epoxy cyclohexylmethyl-3,4-epoxy cyclohexane carboxylate, 3,4-epoxy-1-methyl cyclohexyl-3,4-epoxy-1-methyl hexane carboxylate, 6-methyl-3,4-epoxy cyclohexylmethyl-6-methyl-3,4-epoxy cyclohexane carboxylate, 3,4-epoxy-3-methyl cyclohexylmethyl-3,4-epoxy-3-methyl cyclohexane carboxylate, 3,4-epoxy-5-methyl cyclohexylmethyl-3,4-epoxy-5-methyl cyclohexane carboxylate, 2-(3,4-epoxy cyclohexyl-5,5-spiro-3,4-epoxy) cyclohexane meta dioxane, bis(3,4-epoxy cyclohexylmethyl) adipate, 3,4-epoxy-6-methyl cyclohexyl carboxylate, methylene bis(3,4-epoxy cyclohexane ), dicyclopentadienediepoxide, ethylene bis (3,4-epoxy cyclohexane carboxylate) and the like; polyglycidyl ethers of aliphatic multivalent alcohols or alkylene oxide adducts thereof, for instance, 1,4-butanedioldiglycidyl ether, 1,6-hexanedioldiglycidyl ether, hydrogenated bisphenol A diglycidyl ether, triglycidyl ethers of glycerin, triglycidyl ethers of trimethylol propane, tetraglycidyl ethers of sorbitol, hexaglycidyl ethers of dipentaerythritol and the like; polyglycidyl esters of aliphatic polybasic acid, for instance, diglycidyl tetrahydrophthalate, diglycidyl hexahydrophthalate, diglycidyl hexahydro-3-methyl phthalate, and the like; epoxidized products of unsaturated long chain compounds, such as, epoxidized soybean oil and epoxidized polybutadiene; homopolymers of glycidyl (meth) acrylate or co-polymers of these and other unsaturated monomers, and the like, furthermore, multifunctional epoxides having a skeleton of dimethylsiloxane such as those described in Journal of Polym. Sci., Part A, Polym. Chem.,Vol. 28, 497 (1990), and elsewhere, can be cited.

Examples of oxetanes include those well known in the prior art, and, for instance, 3-ethyl-3-hydroxymethyl oxetane, (3-ethyl-3-oxetanylmethoxy) methylbenzene, [1-(3-ethyl-3-oxetanylmethoxy) ethyl]phenyl ether, isobutoxy methyl (3-ethyl-3-oxetanylmethyl) ether, isobornyloxy ethyl (3-ethyl-3-oxetanylmethyl) ether, isobornyl (3-ethyl-3-oxetanylmethyl) ether, 2-ethyl hexyl (3-ethyl-3-oxetanylmethyl) ether, ethyldiethylene glycol (3-ethyl-3-oxetanylmethyl) ether, dicyclopentenyloxy ethyl (3-ethyl-3-oxetanylmethyl) ether, dicyclopentenyl (3-ethyl-3-oxetanylmethyl) ether, tetrahydrofurfuryl (3-ethyl-3-oxetanylmethyl) ether, tetrabromo phenyl (3-ethyl-3-oxetanylmethyl) ether, 2-tetrabromo phenoxy ethyl (3-ethyl-3-oxetanylmethyl) ether, tribromo phenyl (3-ethyl-3-oxetanylmethyl) -ether, 2-tribromo phenoxy ethyl (3-ethyl-3-oxetanylmethyl) ether, 2-hydroxyethyl (3-ethyl-3-oxetanylmethyl) ether, 2-hydroxy propyl (3-ethyl-3-oxetanylmethyl) ether, butoxy ethyl (3-ethyl-3-oxetanylmethyl) ether, pentachlorophenyl (3-ethyl-3-oxetanylmethyl) ether, pentabromo phenyl (3-ethyl-3-oxetanylmethyl) ether, bornyl (3-ethyl-3-oxetanylmethyl) ether, 3,7-bis(3-oxetanyl)-5-oxa-nonane, 3,3'-(1,3-(2-methylenyl) propanediyl bis (oxy methylene) ) bis-(3-ethyl oxetane), 1,4-bis[(3-ethyl-3-oxetanylmethoxy) methyl]benzene, 1,2-bis[(3-ethyl-3-oxetanylmethoxy) methyl]ethane, 1,3-bis [(3-ethyl-3-oxetanylmethoxy) methyl]propane, ethylene glycol bis (3-ethyl-3-oxetanylmethyl) ether, dicyclopentenyl bis (3-ethyl-3-oxetanylmethyl) ether, triethylene glycol bis (3-ethyl-3-oxetanylmethyl) ether, tetraethylene glycol bis (3-ethyl-3-oxetanylmethyl) ether, tricyclodecanediyldimethylene (3-ethyl-3-oxetanylmethyl) ether, trimethylol propane tris(3-ethyl-3-oxetanylmethyl) ether, 1,4-bis(3-ethyl-3-oxetanylmethoxy) butane, 1,6-bis(3-ethyl-3-oxetanylmethoxy) hexane, pentaerythritol tris (3-ethyl-3-oxetanylmethyl) ether, pentaerythritol tetrakis (3-ethyl-3-oxetanylmethyl) ether, polyethyleneglycol bis (3-ethyl-3-oxetanylmethyl) ether, dipentaerythritol hexakis (3-ethyl-3-oxetanylmethyl) ether, dipentaerythritol pentakis (3-ethyl-3-oxetanylmethyl) ether, dipentaerythritol tetrakis (3-ethyl-3-oxetanylmethyl) ether, 3-ethyl-3-phenoxy methyl oxetane, 3-ethyl-3-(4-methylphenoxy) methyl oxetane, 3-ethyl-3-(4-fluorophenoxy) methyl oxetane, 3-ethyl-3-(1-naphthoxy) methyl oxetane, 3-ethyl-3-(2-naphthoxy) methyl oxetane, 3-ethyl-3-{[3-(ethoxy silyl) propoxy]methyl}oxetane, oxetanyl silsesquioxane, phenol novolac oxetane and the like, may be cited.

Examples of the ethylenically unsaturated compounds include those well known in the prior art having cationic polymerizability, and, for instance, aliphatic monovinyl ethers, such as, methylvinyl ether, ethylvinyl ether, butylvinyl ether, isobutylvinyl ether, cyclohexylvinyl ether, 2-chloroethylvinyl ether, 2-hydroxyethylvinyl ether, 4-hydroxy butylvinyl ether, stearyl vinyl ether, 2-acetoxy ethylvinyl ether, diethylene glycol monovinyl ether, 2-ethyl hexylvinyl ether, dodecylvinyl ether, octadecylvinyl ether, allylic vinyl ether, 2-metacryloyloxy ethylvinyl ether and 2-acryloyloxy ethylvinyl ether; aromatic monovinyi ethers, such as, 2-phenoxy ethylvinyl ether, phenylvinyl ether and p-methoxyphenylvinyl ether; multifunctional vinyl ethers, such as, butanediol-1, 4-divinyl ether, triethylene glycoldivinyl ether, 1,4-benzenedivinyl ether, hydroquinone divinyl ether, cyclohexane dimethanol divinyl ether (1,4-bis[(vinyloxy) methyl]cyclohexane), diethylene glycoldivinyl ether, dipropylene glycoldivinyl ether and hexanedioldivinyl ether; styrenes, such as, styrene, α-methyl styrene, p-methoxy styrene and p-tert-butoxy styrene; cationic polymerizable nitrogen-containing monomers, such as, N-vinyl carbazole and N-vinyl pyrrolidone, and the like, can be cited.

Examples of bicycloortho esters include 1-phenyl-4-ethyl-2,6,7-trioxa bicyclo[2.2.2]octane, 1-ethyl-4-hydroxymethyl-2,6,7-trioxa bicyclo-[2.2.2]octane and the like.

Examples of spiro ortho carbonates include 1,5,7,11-tetraoxaspiro[5.5]undecane, 3,9-dibenzyl-1,5,7,11-tetraoxaspiro[5.5]undecane and the like.

Examples of spiro orthoesters include 1,4,6-trioxa spiro [4.4]nonane, 2-methyl-1,4,6-trioxa spiro [4.4]nonane, 1,4,6-trioxa spiro [4.5]decane and the like.

These cationic polymerizable compounds are described in Japanese Patent Application Laid-Open No. H11-060996, Japanese Patent Application Laid-Open No. H09-302269, Japanese Patent Application Laid-Open No. 2003-026993, Japanese Patent Application Laid-Open No. 2002-206017, Japanese Patent Application Laid-Open No. H11-349895, Japanese Patent Application Laid-Open No. H10-212343, Japanese Patent Application Laid-Open No. 2000-119306, Japanese Patent Application Laid-Open No. H10-67812, Japanese Patent Application Laid-Open No. 2000-186071, Japanese Patent Application Laid-Open No. H08-85775, Japanese Patent Application Laid-Open No. H08-134405, "Photo-Polymer Handbook", The Technical Association of Photo Polymers Japan Edition (1989, Kogyo Chosakai), "Technology of UV/EB Curing", Sogo Gijutsu Center Edition (1982, Sogo Gijutsu Center), "UV/EB Curable Materials", RadTech Edition (1992, CMC), "Causes Of UV Curing defects/inhibition and Remedies Therefor", Technical Information Institute Edition (2003, Technical Information Institute), Japan Society of Color Materials, 68, (5), 286-293 (1995), Fine Chemical, 29, (19), 5-14 (2000), and elsewhere.

Among these cationically polymerizable compounds, epoxides, oxetanes and vinyl ethers are preferred and, in particular, alicyclic epoxides and oxetanes are preferrd. In addition, these cationically polymerizable compounds may be used alone, or two or more species may be combined for application.

The proportion for the cationic polymerization initiator of the present invention to be use relative to the above-mentioned cationically polymerizable compound is, usually, 0.05 to 20 parts, and preferably 0.1 to 10 parts per 100 parts of the polymerizable compound; however, adequate proportion for use is determined relative to 100 parts of the cationically polymerizable compound, taking into consideration various factors such as, the nature of the cationically polymerizable compound, types and irradiance level of the energy beams, temperature, curing time, humidity and thickness of the coating film. If the proportion of the cationic polymerization initiator used is smaller than 0.05 part, polymerization of the cationically polymerizable compound becomes insufficient, and if larger than 20 parts, sometimes the characteristics of the cured material decrease due to unreacted cationic polymerization initiator or decomposition products thereof.

Additives can be used as necessary in the curable composition of the present invention, including sensitizers, pigments, fillers, antistatic agents, flame retardants, antifoaming agents, flow adjusters, photostabilizers, solvents, non-reactive resins and radical polymerizable compounds.

As necessary, a sensitizer well known in the prior art can be combined for application with the curable composition of the present invention, in particular for those that are to be cured by irradiation with active energy beams. Examples of such sensitizers are described in Japanese Patent Application Laid-Open No. H11-279212, Japanese Patent Application Laid-Open No. H9-183960 and the like, and, particularly, anthracenes, such as, anthracene, 9,10-dibutoxy anthracene, 9,10-dimethoxy anthracene, 2-ethyl-9,10-dimethoxy anthracene, 2-tert-butyl-9,10-dimethoxy anthracene, 2,3-dimethyl-9,10-dimethoxy anthracene, 9-methoxy-10-methyl anthracene, 9,10-diethoxy anthracene, 2-ethyl-9,10-diethoxy anthracene, 2-tert-butyl-9,10-diethoxy anthracene, 2,3-dimethyl-9,10-diethoxy anthracene, 9-ethoxy-10-methyl anthracene, 9,10-dipropoxy anthracene, 2-ethyl-9,10-dipropoxy anthracene, 2-tert-butyl-9,10-dipropoxy anthracene, 2,3-dimethyl-9,10-dipropoxy anthracene, 9-isopropoxy-10-methyl anthracene, 9,10-dibenzyloxy anthracene, 2-ethyl-9,10-dibenzyloxy anthracene, 2-tert-9,10-dibenzyloxy anthracene, 2,3-dimethyl-9,10-dibenzyloxy anthracene, 9-benzyl oxy-10-methyl anthracene, 9,10-di-α-methylbenzyloxy anthracene, 2-ethyl-9,10-di-α-methylbenzyloxy anthracene, 2-tert-9,10-di-α-methylbenzyloxy anthracene, 2,3-dimethyl-9,10-di-α-methylbenzyloxy anthracene, 9-(α-methylbenzyloxy)-10-methyl anthracene, 9,10-diphenyl anthracene, 9-methoxy anthracene, 9-ethoxy anthracene, 9-methyl anthracene, 9-bromo anthracene, 9-methylthio anthracene and 9-ethylthio anthracene; pyrene; 1,2-benzo anthracene; perylene; tetracene; coronene;thioxanthones, such as, thioxanthone, 2-methyl thioxanthone, 2-ethyl thioxanthone, 2-chloro thioxanthone, 2-isopropyl thioxanthone and 2,4-diethyl thioxanthone; phenothiazine; xanthone; naphthalenes, such as, 1-naphthol, 2-naphthol, 1-methoxy naphthalene, 2-methoxy naphthalene, 1,4-dihydroxy naphthalene, 1,5-dihydroxy naphthalene, 1,6-dihydroxy naphthalene, 2,7-dihydroxy naphthalene, 2,7-dimethoxy naphthalene, 1,1'-thio bis (2-naphthol), 1,1'-bi-(2-naphthol) and 4-methoxy-1-naphthol;ketones, such as, dimethoxy acetophenone, diethoxy acetophenone, 2-hydroxy-2-methyl-1-phenyl propane-1-one, 4'-isopropyl-2-hydroxy-2-methyl-propiophenone, 2-hydroxymethyl-2-methylpropiophenone, 2,2-dimethoxy-1,2-diphenyl ethane-1-one, p-dimethylamino acetophenone, p-tert-butyl dichloroacetophenone, p-tert-butyl trichloroacetophenone, p-azidobenzalacetophenone, 1-hydroxy cyclohexylphenyl ketone, benzoin, benzoin methyl ether, benzoin ethyl ether, benzoin isopropyl ether, benzoin-n-butyl ether, benzoin isobutyl ether, 1-[4-(2-hydroxyethoxy) phenyl]-2-hydroxy-2-methyl-1-propane-1-one, benzophenone, methyl o-benzoyl benzoate, Michier's ketone, 4,4'-bisdiethylamino benzophenone, 4,4'-dichlorobenzophenone and 4-benzoyl-4'-methyldiphenyl sulfide; carbazoles, such as, N-phenyl carbazole, N-ethyl carbazole, poly-N-vinyl carbazole and N-glycidyl carbazole; chrysenes, such as, 1,4-dimethoxy chrysene, 1,4-diethoxy chrysene, 1,4-dipropoxy chrysene, 1,4-dibenzyloxy chrysene and 1,4-di-α-methylbenzyloxy chrysene;phenanthrenes, such as, 9-hydroxy phenanthrene, 9-methoxy phenanthrene, 9-ethoxy phenanthrene, 9-benzyloxy phenanthrene, 9,10-dimethoxy phenanthrene, 9,10-diethoxy phenanthrene, 9,10-dipropoxy phenanthrene, 9,10-dibenzyloxy phenanthrene, 9,10-di-α-methylbenzyloxy phenanthrene, 9-hydroxy-10-methoxy phenanthrene and 9-hydroxy-10-ethoxy phenanthrene may be cited.

When these sensitizers are used, the proportions used are, usually, 0.005 to 20 parts, and preferably 0.01 to 10 parts, per 100 parts of the curable composition of the present invention.

Examples of pigments include those well known in the art, and, for instance, those from the inorganic types, such as, titanium dioxide, iron oxides and carbon black, and those from the organic types, such as, azo pigments, cyanine pigments, phthalocyanine pigments and quinacridone pigments, can be cited.

The proportions for using these pigments, relative to 100 parts of curable composition of the present invention are, usually, 0.1 to 300 parts, and preferably 1 to 200 parts.

Examples of fillers include those well known in the prior art, and, for instance, molten silica, crystalline silica, calcium carbonate, aluminum oxide, aluminum hydroxide, zirconium oxide, magnesium carbonate, mica, talc, calcium silicate, lithium aluminum silicate, and the like may be cited.

When these fillers are used, the proportions used are, usually, 10 to 300 parts, and preferably 30 to 200 parts, per 100 parts of the curable composition of the present invention.

Examples of the antistatic agents include those well known in the prior art, and, for instance, those that are of the nonionic type, such as, glycerin fatty acid esters, polyoxyethylene alkyl ethers, polyoxyethylene alkylphenyl ethers, N,N-bis(2-hydroxyethyl) alkylamine, polyoxyethylene alkylamine, polyoxyethylene alkylamine fatty acid esters and alkyldiethanol amide; those that are of the anionic type, such as, alkyl sulfonate, alkylbenzene sulfonate and alkyl phosphate; those that are cationic type, such as, tetraalkyl ammonium salts and trialkylbenzyl ammonium salts; those that are of the amphoteric type, such as, alkyl betaines and alkyl imidazolium betaines; those that are of the ionic and nonionic macromolecular type, such as, styrene-(meth) acrylate copolymers containing a quaternary ammonium group, styrene-acrylonitrile-maleimide copolymers containing a quaternary ammonium group and polyethylene oxide, polyether ester amide, polyether amide imide, ethylene oxide-epichlorohydrin copolymers, methoxy polyethyleneglycol (meth) acrylate copolymers, and the like may be cited.

When these antistatic agents are used, the proportions used are, usually, 0.01 to 10 parts, and preferably 0.05 to 5 parts, per 100 parts of curable composition of the present invention.

Examples of flame retardants include those well known in prior art, and, for instance, those of the inorganic type, such as, antimony trioxide, antimony pentoxide, tin oxide, tin hydroxide, molybdenum oxide, zinc borate, barium metaborate, red phosphorus, aluminum hydroxide, magnesium hydroxide and calcium aluminate; those of the bromine compound type, such as, tetrabromophthalic anhydride, hexabromobenzene and decabromobiphenyl ether; those of the phosphoric ester type, such as, tris(tribromophenyl) phosphate, may be cited.

When these flame retardants are used, the proportions used are, usually, 0.1 to 20 parts, and preferably 0.5 to 10 parts, per 100 parts of the curable composition of the present invention.

Examples of the antifoaming agents include those well known in the prior art, and, for instance, alcohols, such as, isopropanol, n-butanol, octaethyl alcohol and hexadecyl alcohol; metal soaps, such as, calcium stearate and aluminum stearate; phosphoric esters, such as, tributylphosphate; fatty acid esters, such as, glycerin monolaurate; polyethers, such as, polyalkylene glycol; silicones, such as, dimethyl silicone oil and silica/silicone compounds; and mineral oils in which silica powder has been dispersed, may be cited.

When these antifoaming agents are used, the proportions used are, usually, 0.01 to 10 parts, and preferably 0.05 to 5 parts, per 100 parts of the curable composition of the present invention.

Examples of the flow adjusters include those well known in prior art, and, for instance, hydrogenated castor oils, polyethylene oxides, organic bentonites, colloidal silica, amide waxes, metal soaps, acrylic ester polymer and the like, may be cited.

When these flow adjusters are used, the proportions used are, usually, 0.01 to 10 parts, and preferably 0.05 to 5 parts, per 100 parts of the curable composition of the present invention.

Examples of the photostabilizer include those well known in the prior art, and, for instance, ultraviolet absorbers, such as, benzotriazole, benzophenone, salicylates, cyanoacrylates and derivatives thereof; radical scavengers of which hindered amines are typical; quencher-type ones, such as, nickel complexes and the like may be named.

When these photostabilizers are used, the proportions used are, usually, 0.005 to 40 parts, and preferably 0.01 to 20 parts, per 100 parts of the curable composition of the present invention.

In addition to those solvents already described, a solvent may be used in the curable composition of the present invention in order to dissolve the cationic polymerizable compound or to adjust the viscosity of the composition. As examples of solvents, ethers, such as, anisole, diethyl ether, tetrahydrofuran, 1,4-dioxane and ethyl-tert-butyl ether; aromatic hydrocarbons, such as, toluene, xylene, cumene, ethylbenzene and mesitylene; ketones, such as, acetone, methyl ethyl ketone, isobutyl ketone and cyclohexanone; alcohols, such as, methanol, ethanol, isopropyl alcohol and tert-butyl alcohol; acetonitrile, and the like may be cited.

When these solvents are used, the proportions used are, usually, 10 to 900 parts, and preferably 20 to 500 parts, per 100 parts of the curable composition of the present invention.

In addition, non-reactive resins and/or radical polymerizable compounds can be added to the curable composition of the present invention for improvement of the mechanical properties, the adhesive nature to substrate, and the like, of the cured material. As the non-reactive resins, polyesters, polyvinyl acetates, polyvinyl chlorides, polybutadienes, polycarbonates, polystyrenes, polyvinyl ethers, polyvinyl butyrates, polybutenes, styrene-butadiene block copolymers hydrogenate, copolymer of (meth) acrylate, polyurethanes and the like may be named. The number-average molecular weight of these resins is 1000 to 500,000, and preferably 5000 to 100,000 (the number-average molecular weight was measured by a conventional methods such as GPC).

When they are used, the proportions of use are, usually, 1 to 100 parts, and preferably 5 to 50 parts, per 100 parts of the curable composition of the present invention.

It is desirable to pre-dissolve these resins in the above-mentioned solvents prior to mixing in order to facilitate dissolution into the curable composition of the present invention.

Examples of radical polymerizable compounds are described in "Photo-Polymer Handbook", The Technical Association of Photosensitive Polymers of Japan Edition (1989, Kogyo Chosakai), "Technology of UV/EB Curing", Sogo Gijutsu Center Edition (1982, Sogo Gijutsu Center), "UV/EB Curable Materials", RadTech Study Group Edition (1992, CMC), "Causes Of UV Curing defects/Inhibition and Remedies Therefor", Technical Information Institute Edition (2003, Technical Information Institute) and the like. In particular, monofunctional monomers, such as, methyl (meth) acrylate, ethyl (meth)acrylate, 2-ethylhexyl (meth)acrylate, lauryl (meth)acrylate, 2-hydroxyethyl (meth)acrylate, 1,6-hexanediol mono (meth)acrylate, styrene, vinyl cyclohexene, isobutylene and butadiene; bifunctional monomers, such as, di(meth)acrylate or divinyl benzene of divalent alcohols, such as, ethyleneglycol, propyleneglycol, bisphenol A, hydrogenated or alkylene oxide adducts thereof; multifunctional monomers, such as, (meth)acrylates of polyhydric alcohols, such as, trimethylol propane, glycerin and pentaerythritol or alkylene oxide adducts thereof; epoxy (meth)acrylates obtained by reacting an epoxide, such as, aromatic epoxide, alicyclic epoxide and aliphatic epoxide and (meth)acrylic acid; polyester (meth)acrylates obtained by esterifying with (meth)acrylic acid and the polyester of the hydroxy terminus obtained from an aromatic polybasic acid, such as, phthalic acid, isophthalic acid, terephthalic acid, trimellitic acid or pyromellitic acid, or an aliphatic polybasic acid, such as, succinic acid, adipic acid or cebacic acid, and a multivalent alcohol, such as, ethylene glycol, diethylene glycol, polyethyleneglycol, propylene glycol, dipropylene glycol, polypropylene glycol, neopentyl glycol, polytetramethylene glycol, 1,3-butanediol, 1,4-butanediol, 1,6-hexanediol, trimethylol propane, glycerin, pentaerythritol, bisphenol and alkylene oxide adducts thereof; and urethane (meth)acrylates obtained by reaction between a prepolymer of the isocyanate terminus obtained from a multifunctional isocyanate, that is, alicyclic isocyanates, such as, isophoronediisocyanate and dicyclohexylmethanediisocyanate, aliphatic isocyanates, such as, tetramethylenediisocyanate and hexamethylenediisocyanate, aromatic isocyanates, such as, toluenediisocyanate, phenylenediisocyanate and diphenyl methanediisocyanate, and a multivalent alcohol, such as, ethylene glycol, diethylene glycol, polyethyleneglycol, propylene glycol, polypropylene glycol, neopentyl glycol, poly tetramethylene glycol, 1,3-butanediol, 1,4-butanediol, 1,6-hexanediol, trimethylol propane, glycerin, pentaerythritol, bisphenol, hydrogenated bisphenol and polycaprolactone diol, polyester diol and polycarbonate diol, and a hydroxy group-containing (meth)acrylate, such as, 2-hydroxyethyl (meth)acrylate, 2-hydroxy propyl (meth)acrylate, 4-hydroxy butyl (meth)acrylate and tri (meth)acrylate of pentaerythritol, and the like, may be cited.

When these radical polymerizable compounds are used, the proportions of use are, usually, 1 to 100 parts, and preferably 5 to 50 parts, per 100 parts of the curable composition of the present invention.

When using the aforementioned radical polymerizable compound, in order to increase the molecular weights thereof by radical polymerization, the use of a radical polymerization initiator that initiates polymerization by heat or light is preferable. Examples of these radical polymerization initiators include those that are well known in prior art, and in regards to heat radical polymerization initiators, organic peroxides, for instance, ketone peroxides, such as, methyl ethyl ketone peroxide and cyclohexanone peroxide, peroxy ketals, such as, 2,2-bis(tert-butyl peroxy) butane and 1,1-bis(tert-butyl peroxy) cyclohexane, hydroperoxides, such as, tert-butyl hydroperoxide, cumene hydroperoxide, dialkylperoxide such as, di-tert-butylperoxide, diacylperoxide, such as, diisobutyrylperoxide, dilauroylperoxide, such as dibenzoylperoxide, peroxydicarbonates, such as, diisopropyl peroxy dicarbonate, peroxy esters, such as, tert-butylperoxy isobutyrate, 2,5-dimethyl-2,5-di (benzoylperoxy) hexane, and the like, and azo compounds, for instance, 1,1'-azobis (cyclohexane-1-carbonitrile), 2,2'-azobisisobutylonitrile, 2,2'-azobis (2,4-dimethyl-4-methoxyvaleronitrile), 2,2'-azobis (2-methylpropion amidine) dihydro chloride, 2,2'-azobis[2-methyl-N-(2-propenyl) propionamidine dihydrochloride, 2,2'-azobis (2-methylpropionate amide), 2,2'-azobis[2-methyl-N-(2-hydroxyethyl) propion amide], 2,2'-azobis (2-methyl propane), 2,2'-azobis (2,4,4-trimethyl pentane), dimethyl 2,2'-azobis (2-methylpropionate), and the like, may be cited.

With regard to photo-radical polymerization initiators, acetophenone series compounds, such as, acetophenone, p-tert-butyl trichloro acetophenone and 2,2-diethoxy acetophenone; methyl benzophenone series compounds, such as, benzophenone, methyl o-benzoyl benzoate and 4-benzoyl-4'-methyldipheny sulfide; Michler's ketone series compounds, such as, 4,4'-bis(dimethylamino) benzophenone and 4,4'-bis(diethylamino) benzophenone; benzoin series compounds, such as, benzoin and benzoin methyl ether; thioxanthone series compounds, such as, thioxanthone, 2-methyl thioxanthone, 2-ethyl thioxanthone, 2-chloro thioxanthone, 2-isopropyl thioxanthone and 2,4-diethyl thioxanthone; acyl phosphine series compounds, such as, monoacyl phosphine oxide and bisacyl phosphine oxide, and the like, may be cited.

The proportions of these radical polymerization initiator used are, in general, 0.01 to 20 parts, and preferably 0.1 to 10 parts, with respect to 100 parts of radical polymerizable compound.

The curable composition of the present invention can be prepared by adding to the cationically polymerizable compound a cationic polymerization initiator and, as necessary, the aforementioned various additives, then, at room temperature or, as necessary, under heating, homogeneously mixing and dissolving or kneading by using a three-roller mill, or the like.

The curable composition of the present invention can be cured by irradiation with active energy beams. The active energy beams may be any beams insofar as they have an energy sufficient to induce decomposition of the fluorinated alkyl fluorophosphoric acid salts of onium and transition metal complex of the present invention, and preferably energy beams in the ultraviolet to visible radiation range (from approximately 100 to approximately 800 nm) obtained from low pressure, medium pressure, high pressure or ultrahigh pressure mercury lamps, metal halide lamps, xenon lamps, carbon arc lamps, fluorescent lamps, semiconductor solid-state lasers, argon lasers, He—Cd lasers, KrF excimer lasers, ArF excimer lasers, $F_2$ lasers or the like, is used. Furthermore, it is also possible to use a radiation with a high energy, such as, electron beams or X-rays. The duration of activation energy beam irradiation depends on the intensity of the energy beam and penetrance of the energy beams with respect to the curable composition, and, usually, on the order of 0.1 seconds to 10 seconds suffices at ordinary temperatures. However, when the penetrance of the energy beams is low or when the thickness of the curable composition is thick, it is sometimes preferable to spend more time. Although most of the compositions are cured by cationic polymerization, 0.1 seconds to a few minutes after energy beam irradiation, if necessary, after-curing is possible by heating a few seconds to few hours at room temperature to 150° C. after energy beam irradiation.

In addition, the curable composition of the present invention can also be cured by heating. Heat curing is carried out by heating for a few minutes to a few hours in a range of 50 to 250° C., preferably 80 to 200° C.

As particular applications of the curable composition of the present invention, paints, coatings, inks, positive-type resist, resist film, liquid resist, photosensitive material, adhesive, forming material, molding material, putty, glass fiber impregnating, filler, sealing material, molding encapsulations, material for stereolithography use, and the like may be named.

From the fact that strong acid is produced by light irradiation, the fluorinated alkyl fluorophosphoric acid salts of onium and transition metal complex of the present invention can also be used as photo-acid generators for chemical amplification-type resist materials use, similar to those described in Japanese Patent Application Laid-Open No. 2003-267968, Japanese Patent Application Laid-Open No. 2003-261529, Japanese Patent Application Laid-Open No. 2002-193925, and elsewhere.

Particularly, they can be used as a photo-acid generator for two component chemical amplification-type positive-working resists having as essential constituents a resin that becomes soluble in an alkaline developer solution by the action of an acid, and a photo-acid generator, three component system chemical amplification-type positive-type resists having as essential constituents a resin soluble in an alkaline developer solution, a dissolution inhibitor that becomes soluble in an alkaline developer solution by the action of an acid, and a photo-acid generator, furthermore, chemical amplification-type negative-working resists having as essential constituents a resin soluble in an alkaline developer solution, a crosslinking agent that crosslinks a resin by a heat treatment in the presence of an acid so as to be insoluble in an alkaline developer solution, and a photo-acid generator, and the like.

The fluorinated alkyl fluorophosphoric acid salts of onium and transition metal complex of the present invention may be used alone as photo-acid generators, or used by combining both parties. In addition, other photo-acid generators well known in the prior art can be used for application. The amount of photo-acid generator used is, usually, in the range of 1 to 50% by mass, relative to the resin used in the resist.

EXAMPLES

Hereinafter, the present invention will be further described by way of examples; but the present invention is not limited by these.

Preparation Example 1

Preparation of Potassium Tris (Pentafluoroethyl) Trifluorophosphate

Tris (pentafluoroethyl) difluorophosphorane (gas chromatographic purity: 97%; yield: 72%) was synthesized by electrolytic fluorination of triethyl phosphine according to U.S. Pat. No. 6,264,818.

Then, 18.0 g of potassium fluoride and 600 ml of dimethoxy ethane were added, stirred and suspended in a 1-liter reaction vessel, and 119.0 g of the tris (pentafluoroethyl) difluorophosphorane obtained was added dropwise while keeping the temperature of the solution at 20 to 30° C. After stirring for 24 hours at room temperature, the reaction solution was filtered, dimethoxy ethane was evaporated from the filtrate under reduced pressure to obtain 136.0 g of white powder. This was identified to be potassium tris (pentafluoroethyl) trifluorophosphate by $^{19}F$ and $^{31}P$-NMR.

Preparation Example 2

Preparation of Potassium Tris(heptafluoropropyl) Trifluorophosphate

Tris(heptafluoropropyl) difluorophosphorane (gas chromatographic purity: 89%; yield: 52%) was synthesized by electrolytic fluorination of tris-propyl phosphine according to U.S. Pat. No. 6,264,818.

Then, 18.0 g of potassium fluoride and 600 ml of dimethoxy ethane were added, stirred and suspended in a 1-liter reaction vessel, and 161.0 g of the tris(heptafluoropropyl) difluorophosphorane obtained were added dropwise while keeping the temperature of the solution at 20 to 30° C. After stirring for 24 hours at room temperature, the reaction solution was filtered, dimethoxy ethane was evaporated from the filtrate under reduced pressure to obtain 177.0 g of a white powder. This was identified to be potassium tris(heptafluoropropyl) trifluorophosphate by $^{19}F$ and $^{31}P$-NMR.

Example 1

Preparation of 4-(phenylthio) Phenyldiphenyl Sulfonium Tris (Pentafluoroethyl) Trifluorophosphate After feeding a reaction vessel with 12.12 g of diphenyl sulfoxide, 9.3 g of diphenyl sulfide and 43.0 g of methanesulfonic acid and homogeneously mixing, 7.9 g of acetic anhydride was added dropwise. After 5 hours of reaction at 40 to 50° C., the reaction solution was cooled to room temperature. This reaction solution was added dropwise to a vessel containing 124.5 g of an aqueous solution with 20% in mass of potassium tris (pentafluoroethyl) trifluorophosphate, and extensively stirred at room temperature for 1 hour. The deposited yellow, somewhat viscous, oily product was extracted with 120 g ethyl acetate, the aqueous layer was separated, and furthermore, the organic layer was washed three times with 100 g of water. The solvent was evaporated from the organic layer, and the obtained yellow residue was dissolved by adding 50 g of toluene. In order to eliminate impurities, such as, unreacted starting materials and byproducts, 270 g of hexane were added to this toluene solution, which was stirred extensively at 10° C. for one hour, and then kept standing. As the solution separates into two layers, the upper layer was removed by liquid separation. When 150 g of hexane were added to the remaining lower layer and extensively mixed at room temperature, a pale yellow crystals deposited. They were filtered and dried under reduced pressure to obtain 24.5 g of 4-(phenylthio) phenyldiphenyl sulfonium tris(pentafluoroethyl) trifluorophosphate (yield: 60%; purity: 98% or more).

The 4-(phenylthio) phenyldiphenyl sulfonium tris(pentafluoroethyl) trifluorophosphate obtained was dissolved in the amounts of 10.0 g in 10.0 g of propylene carbonate to prepare a 50% by mass propylene carbonate solution.

Example 2

Preparation of 4-(phenylthio) Phenyldiphenyl Sulfonium Tris (Heptafluoropropyl) Trifluorophosphate In the same manner as in Example 1, excepting replacement of the aqueous solution of 20% by mass of potassium tris(pentafluoroethyl)trifluorophosphate with 163 g of an aqueous solution with 20% by mass of potassium tris(heptafluoropropyl) trifluorophosphate, 26.9 g of 4-(phenylthio) phenyldiphenyl sulfonium tris (heptafluoropropyl) trifluorophosphate were obtained (yield: 54%; purity: at least 98%).

The 4-(phenylthio) phenyldiphenyl sulfonium tris (heptafluoropropyl) trifluorophosphate obtained in an amount of 10 g was dissolved in 10.0 g of propylene carbonate to obtain a propylene carbonate solution of 50% by mass.

Example 3

Synthesis of Di-p-tolyl Iodonium Tris (Pentafluoroethyl) Trifluorophosphate (1) Synthesis of Di-p-tolyl Iodonium Chloride A reaction vessel was fed with 6.35 g of ice and 20 g of sulfuric acid, and cooled to 20° C. Then, 30 g of glacial acetic acid was fed, 41 g of ammonium persulfate were added at 25° C. or lower. After cooling this mixture to 15° C., a mixture of 21.8 g of 4-iodo toluene and 36.8 g of toluene were added dropwise over 2 hours, while keeping the temperature of the solution at 20° C. After stirring at 20° C. for 15 hours, 135 g of water with 35% in mass of sodium chloride was added, the deposited solid product was filtered and washed with saturated sodium chloride water, followed by water washing. After further washing with toluene and hexane, the solid was dried under reduced pressure. By recrystallization from acetone, 15.9 g of di-p-tolyl iodonium chloride were obtained as pale yellow crystals (yield: 46%).

(2) Synthesis of Di-p-tolyl Iodonium Tris(pentafluoroethyl) Trifluorophosphate

When 6.9 g of the di-p-tolyl iodonium chloride obtained above was dissolved in 93 g of methanol, this was added dropwise to a vessel containing 194 g of an aqueous solution with 5% by mass of potassium tris (pentafluoroethyl) trifluorophosphate and stirred for 3 hours at room temperature, a somewhat viscous oily product separated. When the supernatant liquid was removed, the oily product was dissolved by adding 45 g of diethyl ether, then washed with water, and then 185 g of hexane were added to the organic layer, a white solid deposited. This was filtered, washed with hexane and then dried under reduced pressure to obtain 11.8 g of di-p-tolyl iodonium tris (pentafluoroethyl) trifluorophosphate (yield: 78%; purity: at least 98%).

The di-p-tolyl iodonium tris (pentafluoroethyl) trifluorophosphate obtained was dissolved in the amounts of 10.0 g in 10.0 g of propylene carbonate to prepare a solution of propylene carbonate in 50% by mass.

Example 4

Synthesis of ($\eta^5$-cyclopentadienyl) ($\eta^6$-toluene) Fe(II) Tris (Pentafluoroethyl) Trifluorophosphate A reaction vessel was fed with 5.6 g of ferrocene, 20 g of anhydrous aluminum chloride, 1.4 g of aluminum powder and 50 ml of toluene, and the solution was heated under reflux for 16 hours under stirring. The reaction mixture was cooled to room temperature, then dipped in an ice bath, and 50 ml of ice water was added dropwise slowly so that the temperature of the solution did not reach 60° C. The aqueous layer was liquid-separated, and this was washed three times with 10 ml of a mixed solution of toluene/hexane (1:2). When this aqueous layer was added to 100 g of an aqueous solution with 14.5% in mass of potassium tris (pentafluoroethyl) trifluorophosphate and stirred extensively, a yellow oily product separated. This oily product was extracted in 30 ml of dichloromethane and the solvent was removed under reduced pressure to obtain 9.7 g of crystals of the target product ($\eta^5$-cyclopentadienyl) ($\eta^6$-toluene) Fe(II) tris (pentafluoroethyl) trifluorophosphate (yield: 49%; purity: at least 98%).

The ($\eta^5$-cyclopentadienyl) ($\eta^6$-toluene) Fe(II) tris (pentafluoroethyl) trifluorophosphate obtained above was dissolved in an amounts of 8.0 g in 8.0 g of propylene carbonate to obtain a 50% by mass propylene carbonate solution.

Comparative Example 1

Synthesis of Di-p-tolyl Iodonium Hexafluoroantimonate

In the same manner as in Example 3 except for the replacement of 194 g of the aqueous solution of 5% by mass of potassium tris(pentafluoroethyl) trifluorophosphate with 110 g of an aqueous solution of 5% by mass of potassium hexafluoroantimonate, and replacement of 45 g of diethyl ether with 50 g of ethyl acetate, to obtain a 50% by mass propylene carbonate solution of di-p-tolyliodonium hexafluoroantimonate.

Comparative Example 2

Synthesis of Di-p-tolyl Iodonium Tetrakis (Pentafluorophenyl) Borate

Similarly to Example 3 except that 194 g of the aqueous solution with 5% in mass of potassium tris (pentafluoroethyl) trifluorophosphate was replaced with 288 g of aqueous solution with 5% in mass of potassium tetrakis (pentafluorophenyl) borate, a propylene carbonate solution of 50% in mass of di-p-tolyl iodonium tetrakis (pentafluorophenyl) borate was obtained.

Comparative Example 3

Synthesis of Triethylphenacyl Ammonium Tris (Pentafluoroethyl) Trifluorophosphate A reaction vessel was charged with 10.1 g of triethylamine, 19.9 g of phenacylbromide and 200 g of methanol, and they were stirred at room temperature for 6 hours. By evaporating methanol from this solution, 29.9 g of a white crystalline matter were obtained. This was washed with diethyl ether, then dried under reduced pressure, to obtain 24.9 g of an intermediate triethylphenacyl ammonium bromide (yield: 83%).

When a 10 g portion of this was dissolved in 250 g of methanol and added dropwise to a vessel containing 322.4 g of an aqueous solution of 5% by mass of potassium tris (pentafluoroethyl) trifluorophosphate, and the solution was stirred at room temperature for 1 hour, a somewhat viscous oily matter was separated. The supernatant liquid was removed, then, the oily product was dissolved by introducing 30 g of diethyl ether. Then, after washing this diethyl ether solution with water, when 150 g hexane were added to the organic layer, a white solid deposited. This was filtered and washed with hexane, then dried under reduced pressure to obtain 14.0 g of the target triethylphenacyl ammonium tris (pentafluoroethyl) trifluorophosphate (yield: 63%).

The triethylphenacyl ammonium tris (pentafluoroethyl) trifluorophosphate obtained above was dissolved in an amounts of 10.0 g in 10.0 g of propylene carbonate to prepare a propylene carbonate solution of 50% by mass.

Comparative Example 4

Synthesis of Triphenylphenacyl Phosphonium Tris(pentafluoroethyl) Trifluorophosphate Similarly to Comparative Example 3 except that 10.1 g of triethylamine were replaced with 26.2 g of triphenyl phosphine, 200 g of methanol were replaced with 200 g of acetone, and the amount of aqueous solution with 5% in mass of potassium tris (pentafluoroethyl) trifluorophosphate was decreased from 322.4 g to 210 g, a propylene carbonate solution with 50% in mass of triphenylphenacyl phosphonium tris (pentafluoroethyl) trifluorophosphate was prepared.

Comparative Example 5

Synthesis of ($\eta^5$-cyclopentadienyl) ($\eta^6$-toluene) Fe(II) Hexafluoroantimonate Similarly to Example 4 except that 10 ml of mixed solution of toluene/hexane (1:2) were replaced with 10 ml of toluene, 100 g of aqueous solution with 14.5% in mass of potassium tris(pentafluoroethyl) trifluorophosphate were replaced with 150 g of an aqueous solution with 5.1% in mass of ammonium hexafluoroantimonate, a propylene carbonate solution with 50% in mass of ($\eta^5$-cyclopentadienyl) ($\eta^6$-toluene) Fe(II) hexafluoroantimonate was obtained.

Comparative Example 6

Synthesis of ($\eta^5$-cyclopentadienyl) ($\eta^6$-toluene) Fe(II) Hexafluorophosphate Similarly to Example 4 except that 10 ml of the mixed solution of toluene/hexane (1:2) were replaced with 10 ml of toluene, 100 g of aqueous solution with 14.5% in mass of potassium tris(pentafluoroethyl) trifluorophosphate were replaced with 100 g of an aqueous solution with 4.9% in mass of ammonium hexafluorophosphate, a propylene carbonate solution with 50% in mass of ($\eta^5$-cyclopentadienyl) ($\eta^6$-toluene) Fe(II) hexafluorophosphate was obtained.

(Preparation of Curable Composition and Results of Evaluation)

Propylene carbonate solutions with 50% in mass of various onium and transition metal complex salts obtained in Examples 1 to 4 and Comparative Examples 1 to 6 were homogeneously mixed with an alicyclic epoxy resin, which was a cationic polymerizable compound, to prepare a curable composition, and photo-curability and storage stability of each composition were estimated by the methods described below. In addition, the solubility of these salts in a cationic polymerizable compound was estimated. The results are shown in Table 1.

From these, it is clear that the fluorinated alkyl fluorophosphoric acid salts of onium and transition metal complex obtained according to the present invention, have good cationic polymerization initiation capability for epoxy resins, in addition, the storage stability of the curable composition comprising these is excellent. Furthermore, it is clear that the fluorinated alkyl fluorophosphoric acid salts of the present invention have excellent solubility in populsarcationic polymerizable monomers, in particular vinyl ethers, in which cationic polymerization initiators in general are difficult to dissolve.

| No | Synthesis Example | Onium salt or transition metal complex salt Cation | Onium salt or transition metal complex salt Anion | Photocurability | Solubility CHVE (*8) | Solubility EP (*9) | Storage stability |
|---|---|---|---|---|---|---|---|
| 1 | Example-1 | PTDS (*1) | $(CF_3CF_2)_3PF_3$ | A | A | A | A |
| 2 | Example-2 | | $(CF_3CF_2CF_2)_3PF_3$ | A | A | A | A |
| 3 | | | $SbF_6$ (*6) | A | C | A | B |
| 4 | | | $PF_6$ (*7) | D | C | A | A |
| 5 | Example-3 | DTI | $(CF_3CF_2)_3PF_3$ | A | A | A | B (*10) |
| 6 | Comparative Example1 | (*2) | $SbF_6$ | A | C | A | B (*10) |
| 7 | Comparative Example2 | | $B(C_6F_5)_4$ | C | A | A | B (*10) |
| 8 | Comparative Example3 | TEPA (*3) | $(CF_3CF_2)_3PF_3$ | D | A | A | A |
| 9 | Comparative Example4 | TPPP (*4) | $(CF_3CF_2)_3PF_3$ | D | A | A | A |
| 10 | Example-4 | CTFe | $(CF_3CF_2)_3PF_3$ | B | B | A | B |
| 11 | Comparative Example5 | (*5) | $SbF_6$ | B | C | A | C |
| 12 | Comparative Example6 | | $PF_6$ | D | C | A | B |
| | Evaluation criteria | | | Pencil hardness of coating film A: H or higher B: H-B C: B-4B D: liquid | A: uniform, clear B: turbid C: salt separated | | A: below twice viscosity change B: twice or larger viscosity change C: solidified |

(*1): PTDS; 4-(phenylthio)phenyldiphenyl sulfonium
(*2): DTI; di-p-tolyl iodonium
(*3): TEPA; triethylphenacyl ammonium
(*4): TPPP; triphenylphenacyl phosphonium
(*5): CTFe; ($\eta^5$-cyclopentadienyl)($\eta^6$-toluene)Fe(II)
(*6): 4-(phenylthio)phenyldiphenyl sulfonium hexafluoroantimonate (manufactured by San-Apro; product name: CPI-101A)
(*7): 4-(phenylthio)phenyldiphenyl sulfonium hexafluorophosphate (manufactured by San-Apro; product name: CPI-100P)
(*8): CHVE; cyclohexane dimethanol divinyl ether(1,4-bis[(vinyloxy)methyl]cyclohexane, manufactured by ISP; product name: RAPI-CURE CHVE)
(*9): EP; 3,4-epoxy cyclohexylmethyl-3,4-epoxy cyclohexane carboxylate (Manufactured by DOW; product name: UVR-6110)
(*10): result of evaluation after 80° C. × 10 days <Photo-Curability Test Method>

To 100 parts of 3,4-epoxy cyclohexylmethyl-3,4-epoxy cyclohexane carboxylate (produced by DOW; trade name: UVR-6110), 0.5 part of propylene carbonate solution with 50% in mass of various onium and transition metal complex salts obtained in Examples 1 to 4 and Comparative Examples 1 to 6 was added and uniformly mixed to prepare a curable composition. Using an applicator, a polyester film was coated with this composition, irradiated under the conditions described below, then, the pencil hardness of the coating film after 30 minutes was examined (the thickness of the coating film after curing was approximately 40 μm). Higher pencil hardness indicates that the photo-curability of the composition is satisfactory, that is to say, the polymerization initiation capability of the onium or transition metal complex salt with respect to the cationic polymerizable compound is excellent.
(conditions)
  Ultraviolet irradiation apparatus: belt conveyor-type UV irradiation apparatus (manufactured by Eye Graphics)
  Lamp: 2 KW (100 W/cm) parallel light-type metal halide lamp; irradiation distance: 18 cm
  Conveyor speed: 4 m/minute
  Irradiation frequency: once <Solubility Test Method>

To each 100 parts of the cationically polymerizable compound cyclohexane dimethanol divinyl ether (1,4-bis[(vinyloxy)methyl] cyclohexane, manufactured by ISP; product name: RAPI-CURE CHVE) and 3,4-epoxy cyclohexylmethyl-3,4-epoxy cyclohexane carboxylate (same as above), 5 parts of propylene carbonate solution with 50% in mass of various onium and transition metal complex salts obtained in Examples 1 to 4 and Comparative Examples 1 to 6 were added and uniformly stirred at room temperature, then solubility was estimated by the appearance of the mixed solution. When the solubility of the onium and transition metal complex salts with respect to the cationically polymerizable monomer was good, the mixed solution was uniform and clear; while, if the solubility was poor, the mixed solution was turbid, and furthermore, salts became separated.

<Storage Stability Test Method>

To 100 parts of 3,4-epoxy cyclohexylmethyl-3,4-epoxy cyclohexane carboxylate (same as above), 3 parts of propylene carbonate solution with 50% in mass of various onium and transition metal complex salts obtained in Examples 1 to 4 and Comparative Examples 1 to 6 were added and homogeneously mixed. Immediately after preparation of this composition and after one month storage at 80° C., viscosity was measured at 25° C., and the storage stability was estimated by the extent of increase in the viscosity. The smaller the ratio of increase in viscosity, the better the storage stability of the composition. Note that, for those having di-p-tolyl iodonium (DTI) as the cationic moiety, the same measurements were undertaken with the sample after 10 days storage at 80° C. to estimate the storage stability.

INDUSTRIAL APPLICABILITY

The fluorinated alkyl fluorophosphoric acid salts of onium and transition metal complex of the present invention can be used satisfactorily as a cationic polymerization initiator and a photo-acid generator for paints, coatings, inks, resists (positive-working resists, chemical amplification-type resists and negative-working resists), resist film, photosensitive material, adhesive, forming material, molding material, putty, glass fiber impregnant, filler, sealing material, molding encapsulation and material for stereolithography use.

The invention claimed is:

1. An onium salt of a fluoroalkyl fluorophosphoric acid represented by the general formula (1):

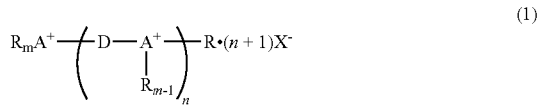  (1)

in the formula (1), A is an element of an atomic valence m belonging to the VIA Group to the VIIA Group (CAS notation), m is 1 or 2, n is an integer of 0-3 which gives the number of recurring units of the structure in the parenthesis; R is an unsubstituted or substituted organic group bonded to A and represents an aryl group having 6-30 carbon atoms, a heterocyclic group having 4-30 carbon atoms, an alkyl group having 1-30 carbon atoms, an alkenyl group having 2-30 carbon atoms or an alkyl group having 2-30 carbon atoms and R can further optionally be substituted by at least one kind selected from the group consisting of alkyl, hydroxy, alkoxy, alkylcarbonyl, arylcarbonyl, alkoxycarbonyl, aryloxycarbonyl, arylthiocarbonyl, acyloxy, arylthio, alkylthio, aryl, heterocyclic, aryloxy, alkylsulfinyl, arylsulfinyl, alkylsulfonyl, arylsulfonyl, alkylenoxy, amino, cyano and nitro groups and halogens; the number of R groups is m+n(m−1)+1 and each R can be the same as or can be different from the others; besides, it is optional that two or more R groups form a ring structure including the element A by joining together either directly or through a —O—, —S—, —SO—, —SO$_2$—, —NH—, —NR'—, —CO—, —COO—, —CONH—, alkylene group having 1-3 carbon atoms or phenylene group; the R' here is an alkyl group having 1-5 carbon atoms or an aryl group having 6-10 carbon atoms; D is a structure represented by the general formula (2) given below:

  (2)

in the formula (2), E represents an alkylene group having 1-8 carbon atoms, arylene group having 6-20 carbon atoms or a divalent group of a heterocyclic compound having 8-20 carbon atoms and further E can be substituted by at least one selected from the group consisting of groups of alkyl having 1-8 carbon atoms, alkoxy having 1-8 carbon atoms, aryl having 6-10 carbon atoms, hydroxy, cyano and nitro and halogens; G represents —O—, —S—, —SO—, —SO$_2$—, —NH—, —NR'—, —CO—, —COO—, —CONH—, alkylene group having 1-3 carbon atoms or phenylene group; a is an integer of 0-5; Es of a+1 in number and Gs of a in number wherein each can be the same as or different from the others; R' is the same as before; X⁻ is the counter ion to the onium; the number thereof per one molecule is n+1, of which at least one is a fluoroalkyl fluorophosphoric acid anion represented by the general formula (3) and the rest can be different anions:

  (3)

in the general formula (3), Rf represents an alkyl group of which at least 80% of the hydrogen atoms are substituted by fluorine atoms; b is an integer of 1-5 which gives the number thereof; and Rf groups of b in number each can be the same as or different from the others.

2. The onium salt of a fluoroalkyl fluorophosphoric acid according to claim 1 wherein A is S or I.

3. The onium salt of a fluoroalkyl fluorophosphoric acid according to claim 1 wherein at least one of R groups is an aryl group having 6-30 carbon atoms or a heterocyclic group having 4-30 carbon atoms which can optionally be substituted by at least one kind selected from the group consisting of alkyl, hydroxy, alkoxy, alkylcarbonyl, arylcarbonyl, alkoxycarbonyl, aryloxycarbonyl, arylthiocarbonyl, acyloxy, arylthio, alkylthio, aryl, heterocyclic, aryloxy, alkylsulfinyl, arylsulfinyl, alkylsulfonyl, arylsulfonyl, alkyleneoxy, amino, cyano and nitro groups and halogens.

4. The onium salt of a fluoroalkyl fluorophosphoric acid according to claim 1 wherein all of the R groups of m+n(m−1)+1 in number are each an aryl group having 6-30 carbon atoms or a heterocyclic group having 4-30 carbon atoms which can optionally be substituted by at least one kind selected from the group consisting of alkyl, hydroxy, alkoxy, alkylcarbonyl, arylcarbonyl, alkoxycarbonyl, aryloxycarbonyl, arylthiocarbonyl, acyloxy, arylthio, aryl, heterocyclic, aryloxy, alkylsulfinyl, arylsulfinyl, alkylsulfonyl, arylsulfonyl, alkyleneoxy, amino, cyano and nitro groups and halogens, each of which can be the same as or different from the others.

5. The onium salt of a fluoroalkyl fluorophosphoric acid according to claim 1 wherein D is a group of at least one kind selected from the group consisting of:

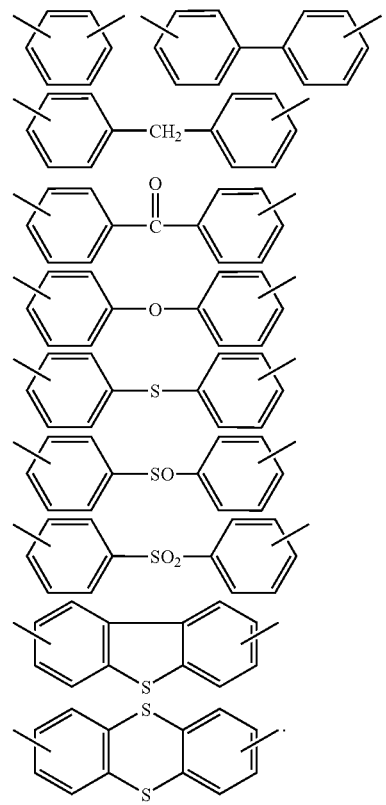

6. The onium salt of a fluoroalkyl fluorophosphoric acid according to claim 1 wherein n is 0 or 1.

7. The onium salt of a fluoroalkyl fluorophosphoric acid according to claim 1 wherein the onium ion of the general formula (1) is triphenyl sulfonium, tri-p-tolyl sulfonium, 4-(phenylthio)phenyl diphenyl sulfonium, bis [4-(diphenylsulfonio)phenyl]sulfide, bis[4-{bis[4-(2-hydroxyethoxy)phenyl]sulfonio}phenyl]sulfide, bis{4-[bis(4-fluorophenyl)sulfonio]phenyl}sulfide, 4-(4-benzoyl-2-chlorophenylthio)phenyl bis(4-fluorophenyl) sulfonium, 4-(4-benzoylphenylthio)phenyl diphenyl sulfonium, 7-isopropyl-9-oxo-10-thia-9,10-dihydroanthracen-2-yl di-p-tolyl sulfonium, 7-isopropyl-9-oxo-10-thia-9,10-dihydroanthracen-2-yl diphenyl sulfonium, 2-[(di-p-tolyl)sulfonio]thioxanthone, 2-[(diphenylsulfonio) thioxanthone, 4-[4-(4-tert-butylbenzoyl)phenylthio]phenyl di-p-tolyl sulfonium, 4-(4-benzoylphenylthio)phenyl diphenyl sulfonium, 5-(4-methoxyphenyl) thiaanthrenium, 5-phenylthiaanthrenium, diphenyl phenacyl sulfonium, 4-hydroxyphenyl methyl benzyl sulfonium, 2-naphthyl methyl (1-ethoxycarbonyl)ethyl sulfonium, 4-hydroxyphenyl methyl phenacyl sulfonium, octadecyl methyl phenacyl sulfonium, diphenyl iodonium, di-p-tolyl iodonium, bis(4-dodecylphenyl) iodonium, bis(4-methoxyphenyl) iodonium, 4-octyloxyphenyl phenyl iodonium, bis(4-decyloxyphenyl) iodonium, 4-(2-hydroxytetradecyloxy)phenyl phenyl iodonium, 4-isopropylphenyl (p-tolyl) iodonium or 4-isobutylphenyl (p-tolyl) iodonium.

8. The onium salt of a fluoroalkyl fluorophosphoric acid according to claim 1 wherein the Rf in the fluoroalkyl fluorophosphoric acid anion represented by the formula (3) has 1-8 carbon atoms and the proportion of the hydrogen atoms substituted by fluorine atoms is at least 90%.

9. The onium salt of a fluoroalkyl fluorophosphoric acid according to claim 1 wherein the Rf in the fluoroalkyl fluorophosphoric acid anion represented by the formula (3) is a straight-chain or branched perfluroalkyl group having 1-4 carbon atoms.

10. A cationic polymerization initiator consisting of at least one kind selected from the onium salt of a fluoroalkyl fluorophosphoric acid according to claim 1.

11. A curable composition consisting of the cationic polymerization initiator according to claim 10 and a cationically polymerizable compound.

12. A cured material formed by curing the curable composition according to claim 11.

13. The onium salt of a fluoroalkyl fluorophosphoric acid according to claim 1 wherein the fluoroalkyl fluorophosphoric acid anion represented by the formula (3) is $[(CF_3CF_2)_3PF_3]^-$, $[((CF_3)_2CF)_3PF_3]^-$, $[(CF_3CF_2CF_2)_3PF_3]^-$, $[((CF_3)_2CF)_2PF_4]^-$, $[((CF_3)_2CFCF_2)_3PF_3]^-$ or $[((CF_3)_2CFCF_2)_2PF_4]^-$.

* * * * *